(12) United States Patent
Von Arx et al.

(10) Patent No.: US 7,072,718 B2
(45) Date of Patent: Jul. 4, 2006

(54) ANTENNA SYSTEMS FOR IMPLANTABLE MEDICAL DEVICE TELEMETRY

(75) Inventors: Jeffrey A. Von Arx, Minneapolis, MN (US); Prashant Rawat, Blaine, MN (US); William R. Mass, Maple Grove, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 566 days.

(21) Appl. No.: 10/309,337

(22) Filed: Dec. 3, 2002

(65) Prior Publication Data

US 2004/0106967 A1    Jun. 3, 2004

(51) Int. Cl.
    *A61N 1/37* (2006.01)
(52) U.S. Cl. .......................................... 607/60; 607/32
(58) Field of Classification Search ............ 607/30–32, 607/60; 128/903
    See application file for complete search history.

(56) References Cited

U.S. PATENT DOCUMENTS

| | | | | |
|---|---|---|---|---|
| 4,539,710 A | * | 9/1985 | Dinsmore | 455/134 |
| 4,562,841 A | | 1/1986 | Brockway et al. | 128/419 PG |
| 5,113,869 A | | 5/1992 | Nappholz et al. | 128/696 |
| 5,342,408 A | * | 8/1994 | deCoriolis et al. | 607/32 |
| 5,861,019 A | | 1/1999 | Sun et al. | 607/60 |
| 6,009,350 A | | 12/1999 | Renken | 607/32 |
| 6,009,878 A | | 1/2000 | Weijand et al. | 128/899 |
| 6,115,636 A | * | 9/2000 | Ryan | 607/60 |
| 6,167,312 A | | 12/2000 | Goedeke | 607/60 |
| 6,169,925 B1 | | 1/2001 | Villaseca et al. | 607/60 |
| 6,240,317 B1 | | 5/2001 | Villaseca et al. | 607/60 |
| 6,305,381 B1 | | 10/2001 | Weijand et al. | 128/899 |
| 6,456,256 B1 | | 9/2002 | Amundson et al. | 343/873 |
| 6,463,329 B1 | | 10/2002 | Goedeke | 607/60 |
| 6,488,704 B1 | | 12/2002 | Connelly et al. | 623/1.15 |
| 6,716,165 B1 | * | 4/2004 | Flanders et al. | 600/301 |
| 6,844,854 B1 | * | 1/2005 | Johnson et al. | 343/702 |

FOREIGN PATENT DOCUMENTS

EP         1062984        12/2000

OTHER PUBLICATIONS

Amundson, Mark D., et al., "Circumferential Antenna for an Implantable Medical Device", U.S. Appl. No. 10/252,494, filed Sep. 23, 2002, 17 pgs.
Mass, William R., et al., "Split-Can Dipole Antenna for an Implantable Medical Device", U.S. Appl. No. 09/761,974, filed Jan. 16, 2001, 12 pgs.

(Continued)

*Primary Examiner*—George Manuel
*Assistant Examiner*—Nicole R. Kramer
(74) *Attorney, Agent, or Firm*—Schwegman, Lundberg, Woessner & Kluth, P.A.

(57) ABSTRACT

An implantable medical device system includes an implanted device communicating with an external device via telemetry. The implanted device and the external device each have a telemetry module connected to an antenna system to support a radio-frequency (RF) telemetry link. The antenna system of the external device has a manually or automatically controllable directionality. The controllable directionality is achieved, for example, by using two or more directional antennas, one non-directional antenna and one or more directional antennas, or an electronically steerable phased-array directional antenna.

48 Claims, 17 Drawing Sheets

OTHER PUBLICATIONS

Von Arx, Jeffrey A., et al., "Antenna for an Implantable Medical Device", U.S. Appl. No. 09/798,249, filed Mar. 2, 2001, 17 pgs.

Von Arx, Jeffrey A., et al., "Telemetry Apparatus and Method for an Implantable Medical Device", U.S. Appl. No. 09/727,093, filed Nov. 30, 2000, 15 pgs.

* cited by examiner

ANTENNA SYSTEMS FOR IMPLANTABLE MEDICAL DEVICE TELEMETRY

TECHNICAL FIELD

This document relates generally to implantable medical devices and particularly, but not by way of limitation, to such a device including a telemetry system allowing communication with an external device.

BACKGROUND

Medical devices are implanted in human bodies for monitoring physiological conditions, diagnosing diseases, treating diseases, or restoring functions of organs or tissues. Examples of such implantable medical devices include cardiac rhythm management systems, neurological stimulators, neuromuscular stimulators, and drug delivery systems. Because such a device may be implanted in a patient for a long time, the size and power consumption of the device are inherently constrained. Consequently, an implantable device may depend on an external system to perform certain functions. Communication between the implantable device and the external system is referred to as telemetry. Examples of specific telemetry functions include programming the implantable device to perform certain monitoring or therapeutic tasks, extracting an operational status of the implantable device, transmitting real-time physiological data acquired by the implantable device, and extracting physiological data acquired by and stored in the implantable device.

One particular example of implantable medical devices is a cardiac rhythm management device implanted in a patient to treat irregular or other abnormal cardiac rhythms by delivering electrical pulses to the patient's heart. Such rhythms result in diminished blood circulation. Implantable cardiac rhythm management devices include, among other things, pacemakers, also referred to as pacers. Pacemakers are often used to treat patients with bradyarrhythmias, that is, hearts that beat too slowly or irregularly. Such pacemakers may coordinate atrial and ventricular contractions to improve the heart's pumping efficiency. Implantable cardiac management devices also include defibrillators that are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias, that is, hearts that beat too quickly. In addition to pacemakers and defibrillators, implantable cardiac rhythm management systems also include, among other things, pacer/defibrillators that combine the functions of pacemakers and defibrillators, drug delivery devices, and any other implantable systems or devices for diagnosing or treating cardiac arrhythmias.

An implantable cardiac rhythm management device typically communicates with an external device referred to as a programmer via telemetry. One type of such telemetry is based on inductive coupling between two closely-placed coils using the mutual inductance between these coils. This type of telemetry is referred to as inductive telemetry or near-field telemetry because the coils must be closely situated for obtaining inductively coupled communication. One example of such an inductive telemetry is discussed in Brockway et al., U.S. Pat. No. 4,562,841, entitled "PROGRAMMABLE MULTI-MODE CARDIAC PACEMAKER," assigned to Cardiac Pacemakers, Inc., the disclosure of which is incorporated herein by reference in its entirety.

In one example of inductive telemetry, an implantable device includes a first coil and a telemetry circuit, both sealed in a metal housing (referred to as a "can"). The external programmer provides a second coil in a wand that is electrically connected to the programmer. During device implantation, a physician evaluates the patient's condition, such as by using the implanted device to acquire real-time physiological data from the patient and communicating the physiological data in real-time to the external programmer for processing and/or display. The physician may also program the implantable device, including selecting a pacing or defibrillation therapy mode, and parameters required by that mode, based on the patient's condition and needs. The data acquisition and device programming are both performed using the inductive telemetry. If the patient's condition is stable after implantation, he or she needs no attention from the physician or other caregiver until a scheduled routine follow-up. During a routine follow-up, for example, the physician reviews the patient's history with the implantable device, re-evaluates the patient's condition, and re-programs the implantable device if necessary.

One problem with inductive telemetry is its requirement that the two coils are closely placed. This typically requires placing the wand on the body surface over the implantable device. Because the wand is electrically connected to the programmer using a cable, the inductive telemetry limits the patient's mobility.

To improve communication range and patient mobility, a far-field radio-frequency (RF) telemetry may be used, in which an RF transceiver in the implantable device is used to communicate with an RF transceiver in the external programmer. With a far-field RF telemetry, the patient is typically free of any body surface attachment that limits mobility. However, the far-field RF telemetry between the implantable device and the external programmer may operate in an environment where one or more sources of interferences exist. Such sources of interferences include, for example, magnetic resonance imaging (MRI) machines, cellular phones, and other devices emitting electromagnetic waves. Such sources of interferences may also include another pair of implantable cardiac rhythm management device and external programmer communicating via far-field RF telemetry operating at the same or similar frequencies.

For these and other reasons, there is a need for ensuring the quality of far-field RF telemetry between an external system and an implanted device when interference is present.

SUMMARY

An implantable medical device system includes an implanted device communicating with an external device via telemetry. The implanted device and the external device each have a telemetry module connected to an antenna system to support an RF telemetry link. The antenna system of the external device has a manually or automatically controllable directionality. The controllable directionality is achieved, for example, by using two or more directional antennas, one non-directional antenna and one or more directional antennas, or an electronically steerable phased-array directional antenna.

In one embodiment, a system for communicating with an implantable medical device includes an external device that is coupled to the implantable medical device via RF telemetry. The external device includes a transceiver, an antenna system, an antenna interface circuit, and a directionality controller. The antenna system includes at least two antennas each having a predetermined directionality characteristic. The antenna interface circuit electrically connects the transceiver and the antenna system. The directionality controller connects to the antenna interface circuit and controls a directionality of the antenna system.

In one embodiment, one or more RF signals are received from an implantable medical device using one or more antennas of an antenna system, where the one or more antennas each have a predetermined directionality characteristic. A quality of each of the one or more RF signals is analyzed. A directionality of the antenna system is controlled based on an outcome of the RF signal quality analysis.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, antennas and antenna systems for a medical device that communicates with an implantable medical device via telemetry. The present methods and apparatuses will be described in applications involving implantable cardiac rhythm management systems such as systems including pacemakers, cardiac resynchronization therapy (CRT) devices, cardioverter/defibrillators, and pacer/defibrillators. However, it is to be understood that the present methods and apparatuses may be employed in other types of implantable medical devices, including, but not being limited to, neurological stimulators, neuromuscular stimulators, drug delivery systems, and various types of physiological signal monitoring devices.

Figure 1:
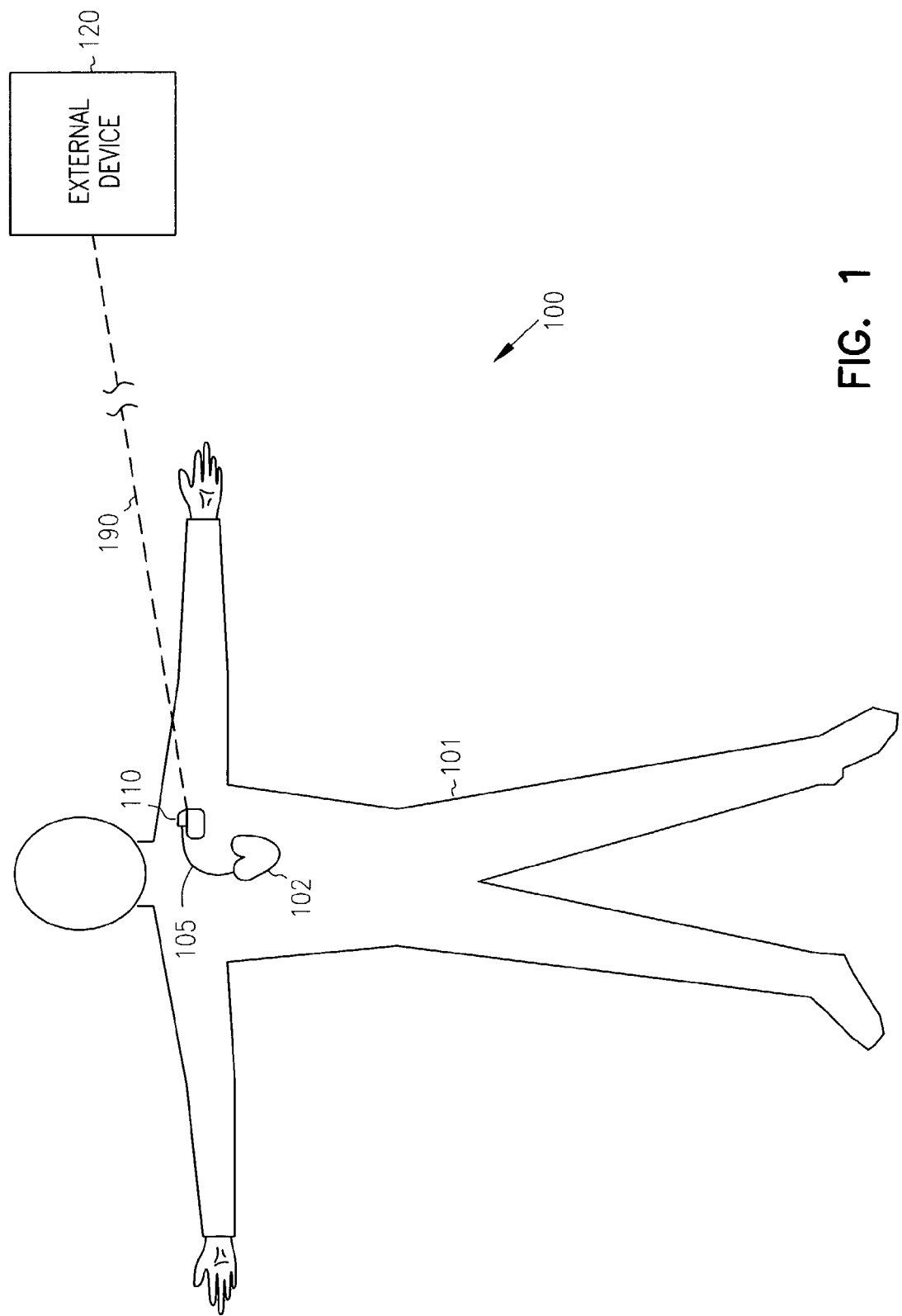
FIG. 1 is a schematic illustration of an embodiment of portions of an implantable medical device system and portions of an environment in which it is used.

FIG. 1 is a schematic illustration of an embodiment of portions of an implantable medical device system 100 and portions of an environment in which it is used. In one embodiment, system 100 is a cardiac rhythm management system including, among other things, an implanted device 110 and an external device 120. Implanted device 110 is implanted within a patient's body 101 and coupled to the patient's heart 102 by a lead system 105. Examples of implanted device 110 include pacemakers, CRT devices, cardioverter/defibrillators, pacemaker/defibrillators, and drug delivery devices. External device 120 provides a user interface for system 100. The user interface allows a physician or other caregiver to interact with implanted device 110 through a wireless telemetry link. In this embodiment, the wireless telemetry link is a radio-frequency (RF) telemetry link 190 supported by RF transceivers residing in implanted device 110 and external device 120. RF telemetry link 190 provides for bi-directional data communication between implanted device 110 and external device 120.

In one embodiment, RF telemetry link 190 provides for data transmission from implanted device 110 to external device 120. This may include, for example, transmitting real-time physiological data acquired by implanted device 110, extracting physiological data acquired by and stored in implanted device 110, extracting therapy history data stored in implanted device 110, and extracting data indicating an operational status of implanted device 110 (e.g., battery status and lead impedance). In a further embodiment, RF telemetry link 190 provides for data transmission from external device 120 to implanted device 110. This may include, for example, programming implanted device 110 to acquire physiological data, programming implanted device 110 to perform at least one self-diagnostic test (such as for a device operational status), and programming implanted device 110 to deliver at least one therapy.

In one embodiment, RF telemetry link 190 is a far-field telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of RF telemetry link 190 (a distance over which data is capable of being wirelessly communicated) is at least ten feet but can be as long as allowed by the communication technology utilized. Unlike an inductive telemetry link using a wand placed near implanted device 110, typically attached to the patient, and electrically connected to external device 120 with a cable, using RF telemetry link 190 frees the patient from any physical restraints caused by the wand and the cable. On the other hand, while a relatively short communication range associated with the inductive telemetry provides for a relatively good immunity to environmental interferences, the relatively long communication range associated with the RF telemetry raises a concern that external device 120 may be sensitive to interferences such as electromagnetic waves radiated from other medical devices, such as MRI machines, and/or personal items such as cellular phones. In addition, several patients carrying the same of similar types of implantable devices may be examined, in the same area or even the same room in a cardiovascular clinic, using the same of similar types of external programmers. Under such circumstances, multiple RF telemetry links may operate within the communication ranges of each other and therefore interfere with the operations of each other. To allow RF telemetry link 190 to operate within such environments, one approach is to control its directionality.

Figure 2:
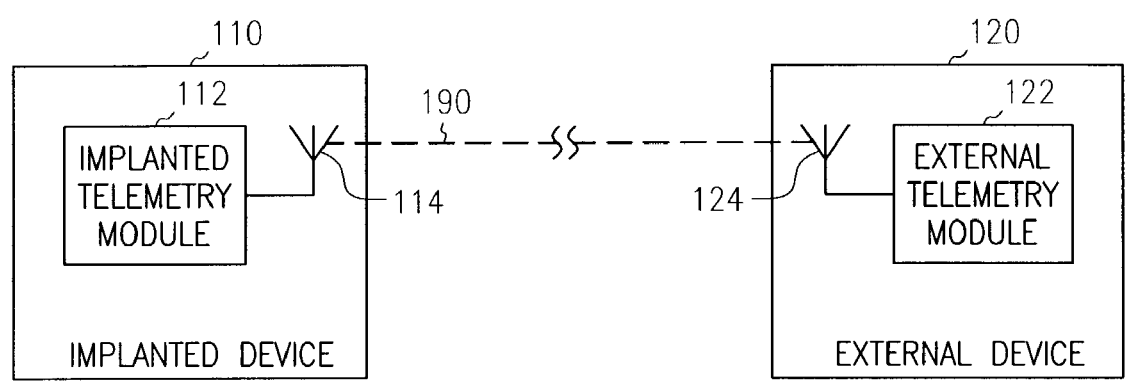
FIG. 2 is a schematic/block diagram illustrating one embodiment of portions of the implantable medical device system with radio-frequency telemetry.

FIG. 2 is a schematic/block diagram illustrating one embodiment of portions of system 100. In this embodiment, implanted device 110 includes an implanted telemetry module 112 and an implanted antenna system 114. External device 120 includes an external telemetry module 122 and an external antenna system 124. Implanted telemetry module 112 and external telemetry module 122 respectively refer to portions of implanted device 110 and external device 120 that communicate with each other via RF telemetry link 190. In one embodiment, implanted telemetry module 112 and external telemetry module 122 each include a transceiver. In one embodiment, implanted antenna system 114 and external antenna system 124 each include a single antenna. In an alternative embodiment, implanted antenna system 114 and external antenna system 124 each include two or more antennas. In another alternative embodiment, implanted antenna system 114 includes a single antenna, and external antenna system 124 comprises two or more antennas.

In one embodiment, implanted telemetry module 112 includes an RF test signal generator to generate an RF test signal and send it to external device 120 via RF telemetry link 190. The RF test signal is used in processes of antenna selection or orientation that are discussed below. In one embodiment, the RF signal is modulated with a predetermined binary code to allow for analysis of data integrity by external telemetry module 122. In one embodiment, the RF signal has a duration of about 50–100 ms. In one embodiment, implanted device 110 has an operation mode being a telemetry testing mode during which the RF test signal is sent to external device 120. In a further embodiment, external device 120 sends a command to implanted device 110 to cause it to operate in the telemetry testing mode. In one embodiment, if external device 120 sends the command during an ongoing telemetry session, the telemetry session is interrupted during the telemetry testing mode and resumed automatically upon completion of the telemetry testing mode operation.

Figure 3:
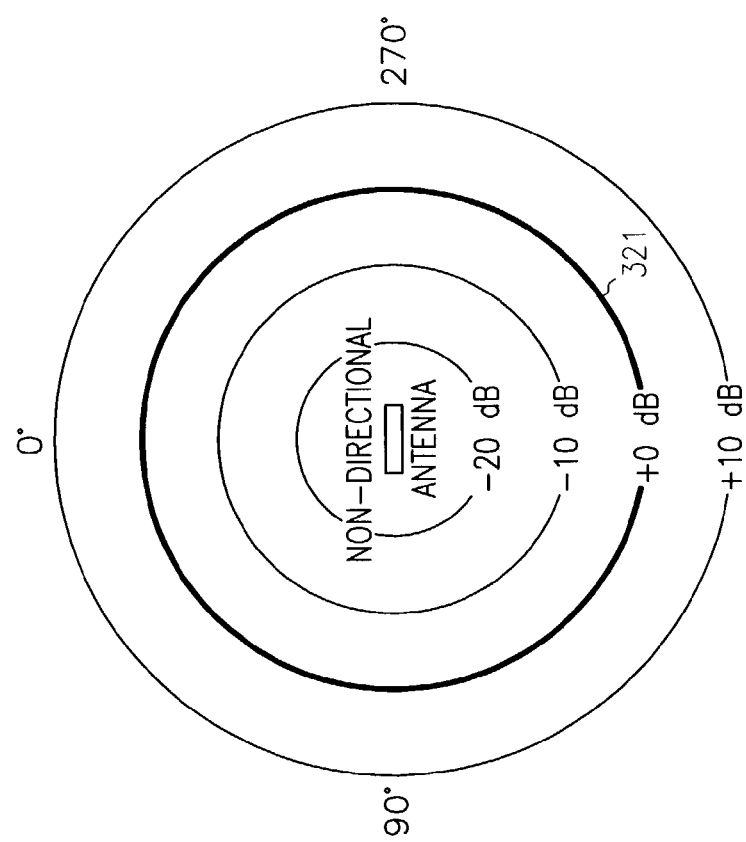
FIG. 3 is an illustration of a radiation pattern of a non-directional antenna.

FIG. 3 is an illustration of a radiation pattern of a non-directional antenna. A non-directional antenna, also referred to as an omnidirectional antenna, is an antenna that transmits electromagnetic waves with equal energy to all directions and/or receives electromagnetic waves equally well from all directions, at least on one plane. A radiation pattern 321 illustrates a directionality characteristic of a non-directional antenna having an approximately uniform gain in all directions in one plane (non-directional plane). In this document, a non-directional antenna refers to an antenna having a predetermined directionality characteristic shown by a radiation pattern with less than 6 dB of signal strength difference between any two directions in the non-directional plane. In one embodiment, the non-directional antenna is a single-dipole antenna. In a further embodiment, the dipole antenna is a single planar dipole antenna and can be printed on a printed circuit board. Radiation pattern 321 illustrates the directionality of the single planar dipole antenna in the plane perpendicular to the planar sides of the antenna. In another embodiment, the non-directional antenna is a loop antenna. In a further embodiment, the loop antenna is formed with a wire or printed on a printed circuit board. Radiation pattern 321 illustrates the directionality of the loop antenna on the plane of the loop. In yet another embodiment, the non-directional antenna is a single monopole antenna. In a further embodiment, the monopole antenna is a single planar monopole antenna and can be printed on a printed circuit board. Radiation pattern 321 illustrates the directionality of the single planar monopole antenna in the plane perpendicular to the planar sides of the antenna.

A non-directional antenna is suitable for use in an environment where no significant interference exists and only a single RF telemetry link is active. No antenna orientation is needed. However, an RF telemetry link may be required to operate in a busy clinical environment where multiple physicians and/or other caregivers evaluate multiple patients simultaneously. This may require several RF telemetry links to operate in the same area or even in the same room. If the several RF telemetry links operate in substantially the same or similar frequency bands, each RF telemetry link using non-directional antenna may interfere with other RF telemetry links. Moreover, electromagnetic energy radiated from sources such as other electronic medical equipment in all directions in the clinical environment may be received by a non-directional antenna as a noise interfering with the RF telemetry supported partially by the non-directional antenna.

Figure 4:
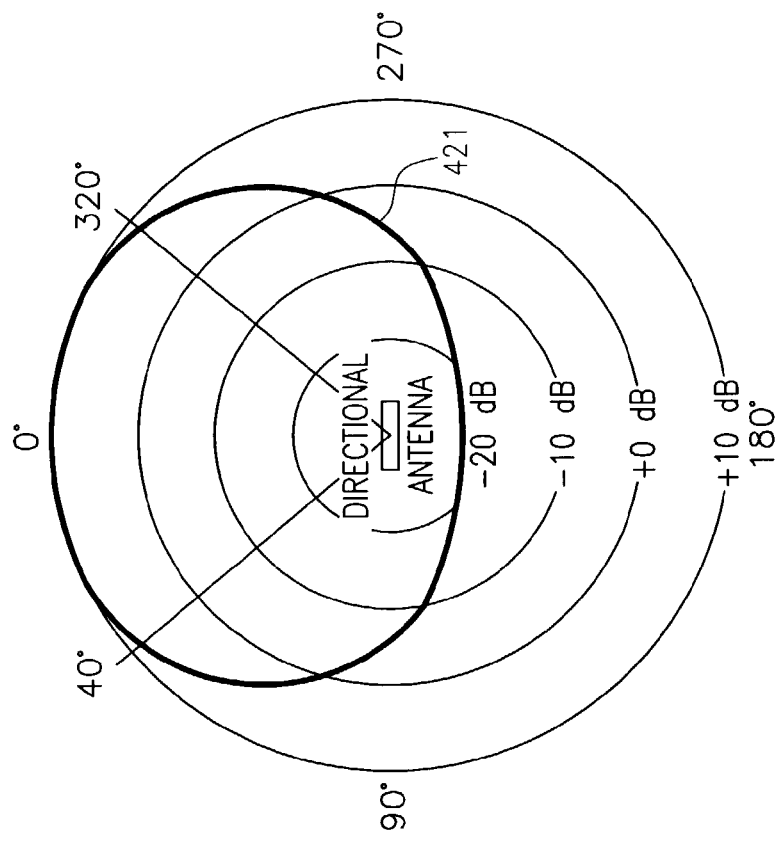
FIG. 4 is an illustration of a radiation pattern of a directional antenna.

FIG. 4 is an illustration of a radiation pattern of a directional antenna. Using a directional antenna provides, among other things, a solution to the problems associated using a non-directional antenna as described above. A directional antenna is an antenna that transmits electromagnetic waves with more energy in one direction than in another direction and/or receives electromagnetic waves more readily from one direction than from another direction in a plane (directional place). In this document, a directional antenna refers to an antenna having a predetermined directionality characteristic shown by a radiation pattern with at least 6 dB of signal strength difference between at least two directions in the directional plane. The directionality (or directionality characteristic) of a directional antenna is measured or defined by beamwidth, which is the angle of the directional antenna's signal coverage, i.e., the angle within which the directional antenna transmits and receive signals. In one embodiment, as illustrated in FIG. 4, a radiation pattern 421 shows a directionality characteristic of a directional antenna having a half-power beamwidth of about 80 degrees in one plane and a highest gain in one direction referred to as the forward direction of the directional antenna. To achieve more directionality, the gain within the half-power beamwidth can be increased by decreasing the beamwidth. In one embodiment, the directional antenna is a planar patch antenna. In a further embodiment, the planar patch antenna is printed on a printed circuit board. Radiation pattern 421 illustrates the directionality of the planar patch antenna in the plane perpendicular to the planar sides of the antenna. In another embodiment, the directional antenna is a slot antenna being a planar conductive patch with a nonconductive hole or rectangular slot. The slot antenna has directionality characteristics similar to those of the patch antenna, as illustrated by radiation pattern 421. Other examples of the directional antenna include, but are not limited to, parabolic reflector (dish) antenna, Uda-Yagi antenna, and helical antenna. In one embodiment, the beamwidth of the directional antenna is chosen based on a compromise among competing design considerations including relative immunity to interferences, ease of aiming, and complexity and cost of circuitry. Narrower beamwidths provide better immunity to interferences. On the other hand, large beamwidths provide ease of aiming or, alternatively, require few patch antennas to cover all directions.

With a limited beamwidth, a directional antenna is less likely to act as a source of interference to RF telemetry links associated with other antennas. This allows multiple RF telemetry links to be established for concurrent communications between multiple pairs of external devices and implanted devices, even within a small area. The directional antenna may also allow a user to locate a source of interference to avoid it. In one embodiment, the user sweeps the directional antenna over all directions to identify sources of interference.

Using the same level of electrical power, a directional antenna achieves higher gain in its forward direction as compared to the uniform gain of a non-directional antenna. This allows a longer communication range allowing external device 120 to communicate with implanted device 110 over a greater distance, as compared with the non-directional antenna, unless it also results in a radiation energy level that exceeds a limitation imposed by pertinent government regulations or other safety standards. A directional antenna generally has a higher signal-to-noise ration (S/N) as compared to a non-directional antenna because of the higher gain applied to a signal and lower gains applied to noises coming from directions outside the directional antenna's beamwidth.

The directionality of RF telemetry link 190 is controllable by controlling a directionality of implanted antenna system 114 and/or a directionality of external antenna system 124. In one embodiment, the directionality of RF telemetry link 190 is controllable by controlling the directionality of external antenna system 124. Implanted device 110 and external device 120 send signals to each other. A noise radiated from a source of interference is received by both implanted device 110 and external device 120. Because body tissue absorbs RF electromagnetic energy, implanted antenna system 114 receives the signals and the noise that are both attenuated by body tissue surrounding implanted device 110. On the other hand, while external antenna system 124 receives signals that are attenuated when being transmitted from implanted device 110 through the surrounding body tissue, the noise radiated from the source of interference is not attenuated by body tissue. Thus, an S/N associated with external antenna system 124 is more degraded by the presence of noise from the source of interference than an S/N associated with implanted antenna system 114. Furthermore, the complexity of implanted device 110 is limited by size and power consumption restraints for an implant. Because many more units of implanted device 110 are produced than units of external device 120, a cost increase associated with implanted device 110 is more of a concern than a cost increase associated with external devices 120. For at least these reasons, controlling the directionality of external antenna system 124 is a more efficient approach as compared to controlling the directionality of implanted antenna system 114 or both antenna systems.

Figure 5:
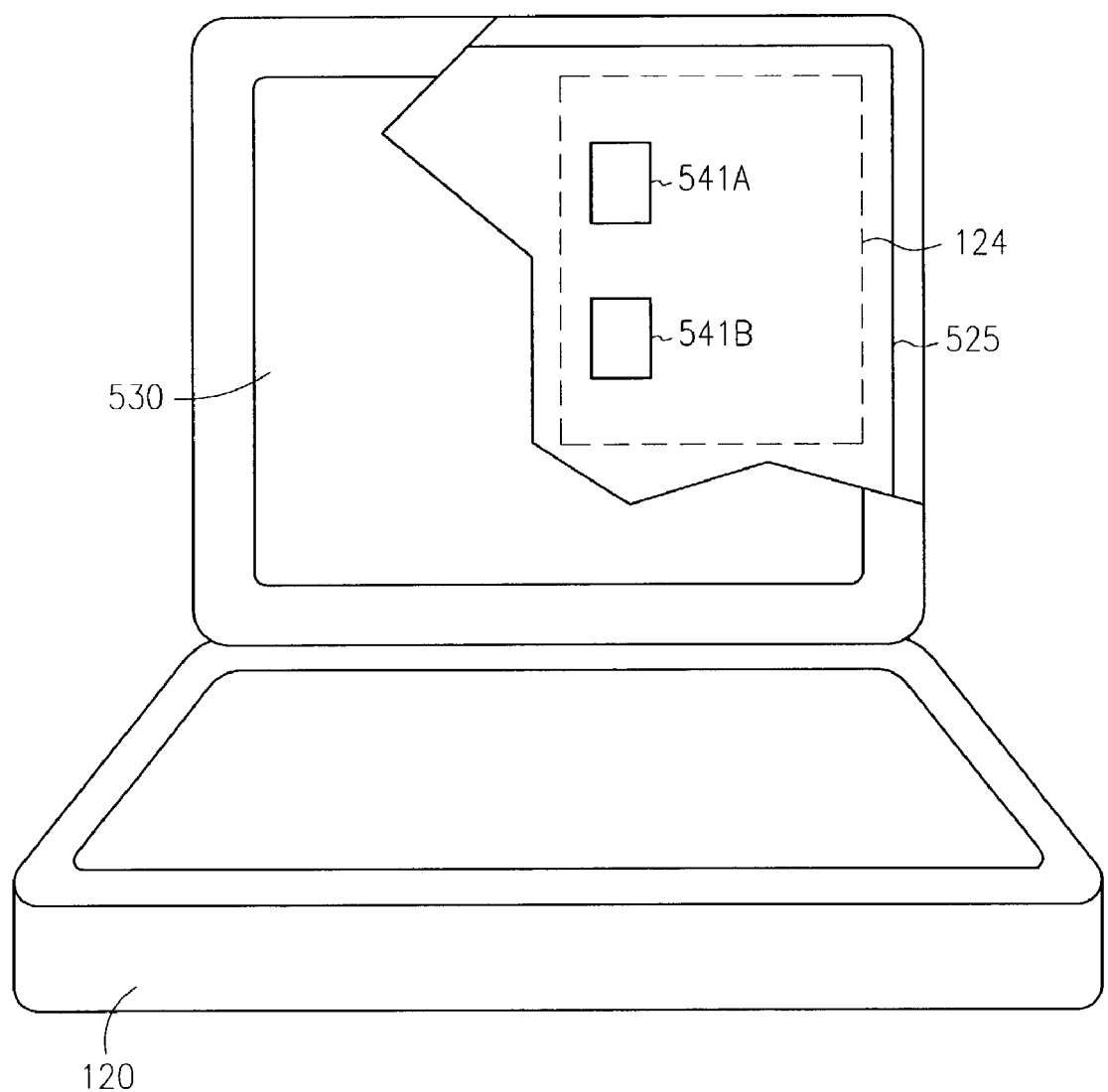
FIG. 5 is a structural diagram illustrating one embodiment of an external device having multiple directional antennas.

FIG. 5 is a structural diagram illustrating one embodiment of an external device having multiple directional antennas. In one embodiment, external device 120 is a computer-based device that controls operation of implanted device 110 and receives data indicative of a patient's physiological and/or pathological conditions, and/or an operational status of implanted device 110, from implanted device 110 through RF telemetry link 190 during an RF telemetry session. In one embodiment, external device 120 is constructed on a notebook computer. In one embodiment, external device 120 is a medical device programmer operated by a user, such as a physician or other caregiver, to communicate with implanted device 110 via RF telemetry link 190. In another embodiment, external device 120 is a monitor communicating with implanted device 110. In one embodiment, the monitor stores the received data for review by the user at a later time. In an alternative embodiment, the monitor relays the received data to a device in a remote location for review by the user. In one embodiment, external device 120 includes a display screen 530, which constitutes a portion of a user interface allowing the user to observe conditions of the patient and to monitor and control the operation of implanted device 110. During a telemetry operation, display screen 530 is set to be about perpendicular to the base of the external device, and hence perpendicular to a floor during the RF telemetry session.

In the embodiment of FIG. 5, antenna system 124 of external device 120 has, by way of example, but not by way of limitation, two directional antennas 541A and 541B, each having a half-power beamwidth of less than or equal to about 180 degrees. In one embodiment, directional antennas 541A and 541B are planar patches. In one embodiment, the planar patches each have a square shape. In an alternative embodiment, the planar patches each have a trapezoidal shape. In one embodiment, the planar patches each have sides that are two to three centimeters long. In another embodiment, directional antennas 541A and 541B are slot antennas each including a planar conductive patch with a nonconductive hole or rectangular slot in it. In one embodiment, directional antenna 541A and 541B are printed on a printed circuit board 525 located behind, and parallel to, display screen 530. Display screen 530 is about perpendicular to the base of the external device, and hence, about perpendicular to the floor during the RF telemetry session. Other examples of directional antennas 541A and 541B include, but are not limited to, parabolic reflector (dish) antenna, Uda-Yagi antenna, and helical antenna. Directional antenna 541A transmits signals to, and receives signals from, substantially all directions behind display screen 530, and directional antenna 541B transmits signals to, and receives signals from, substantially all directions in front of display screen 530. In an alternative embodiment, antenna system 124 has more than two directional antennas for a finer directionality control. In one embodiment, antenna system 124 has three directional antennas each having a half-power beamwidth of about 120 degrees.

In one embodiment, the user selects one of directional antennas 541A and 541B for an RF telemetry session. For example, when directional antenna 541A covers substantially all directions behind display screen 530 and directional antenna 541B covers substantially all directions in front of display screen 530, the user selects directional antenna 541A if the patient is behind the screen, or directional antenna 541B if the patient is in front of the screen. In another embodiment, the user observes the quality of communication, such as indicated by signals received by each of directional antennas 541A and 541B and displayed on display screen 530, to determine which antenna to select. In another embodiment, one of directional antennas 541A and 541B is automatically selected, as discussed below with reference to FIGS. 6 and 7.

In an alternative embodiment, antenna system 124 has a single directional antenna. While using a single directional antenna provides the simplest and least expensive telemetry module 122 having a directional antenna system, the user would have to align external device 120 with implanted device 110. This may require several position adjustments for external device 120 before RF telemetry link 190 is established.

Figure 6:
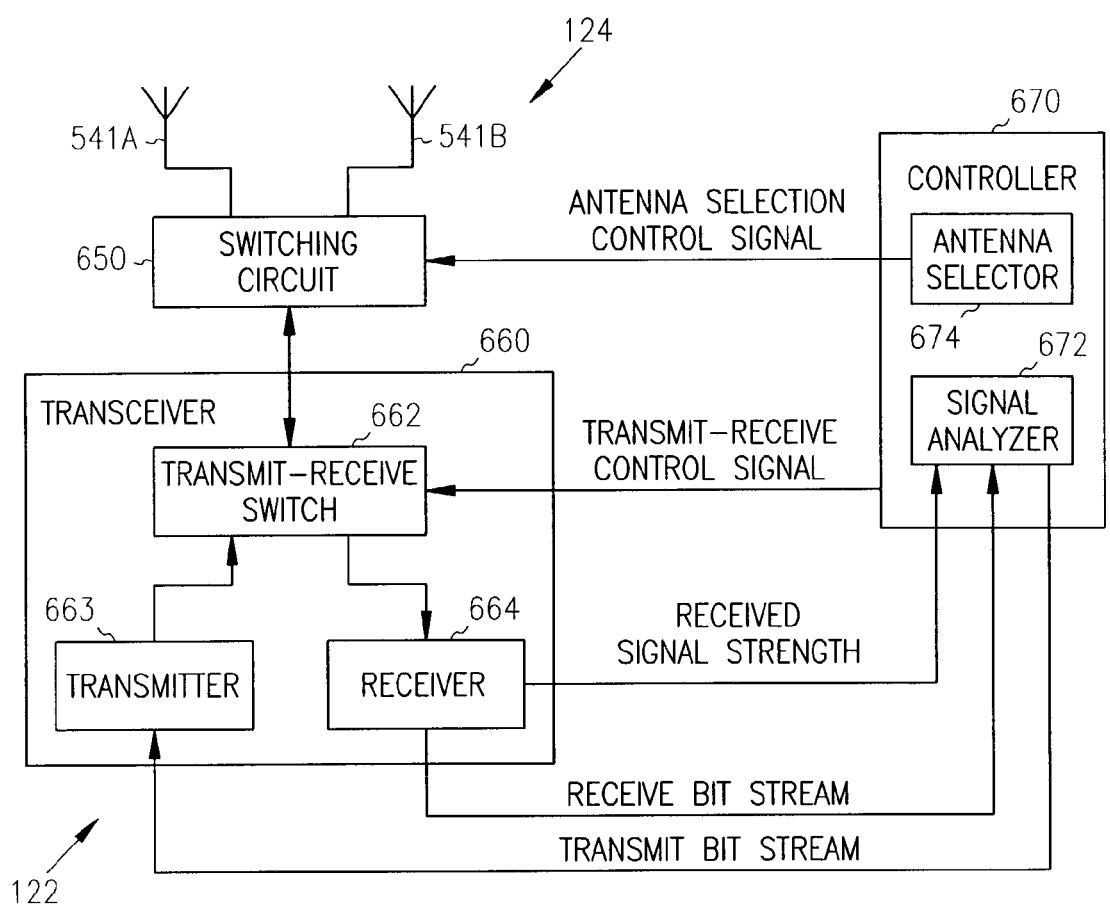
FIG. 6 is a schematic/block diagram illustrating one embodiment of a circuit corresponding to the embodiment of FIG. 5.

FIG. 6 is a schematic/block diagram illustrating one embodiment of a circuit corresponding to the embodiment of FIG. 5. The circuit constitutes portions of external telemetry module 122 and an antenna system 124. External telemetry module 122 includes a transceiver 660, a controller 670, and a switching circuit 650. Transceiver 660 further includes a transmitter 663, a receiver 664, and a transmit-receive switch 662. Transmitter 663 receives data from another portion of external device 120 in a form of a bit stream, modulates an RF carrier signal with the data, and transmits the modulated RF signal to implanted device 110 through antenna system 124. Receiver 664 receives modulated RF signals through antenna system 124, demodulates the modulated RF signal to recover data transmitted from implanted device 110, and sends the recovered data in a format of a bit stream to another portion of external device 120. Transmit-receive switch 662 controls a connection between antenna system 124 and one of transmitter 663 and receiver 664. Transceiver 660 allows for one of transmission and receiving at any instant.

Controller 670 controls whether transceiver 660 transmits or receives RF signals. In the embodiment in which one of directional antennas 541A and 541B is automatically selected, controller 679 also includes a signal analyzer 672 and an antenna selector 674. The signal analyzer analyzes signal quality of the RF signals received through each of directional antennas 541A and 541B. In one embodiment, signal analyzer 672 measures the strength (amplitude) of each of the RF signals received through each of directional antennas 541A and 541B. In a further embodiment, signal analyzer 672 examines integrity of the data recovered by transceiver 660 and generates a data integrity indicator. Antenna selector 674 is a directionality controller of antenna system 124. It controls the directionality of antenna system 124 by selecting one or more of its antennas having different orientation and/or directionality characteristics. In the embodiment of FIG. 6, antenna selector 674 generates an antenna selection control signal based on comparing the outcome of analyzing the signal quality of RF signals received by each of directional antennas 541A and 541B. Switching circuit 650, in response to the antenna selection control signal, makes an electrical connection between transceiver 660 and one of directional antennas 541A and 541B. In one embodiment, switching circuit 650 is a multiplexer.

Figure 7:
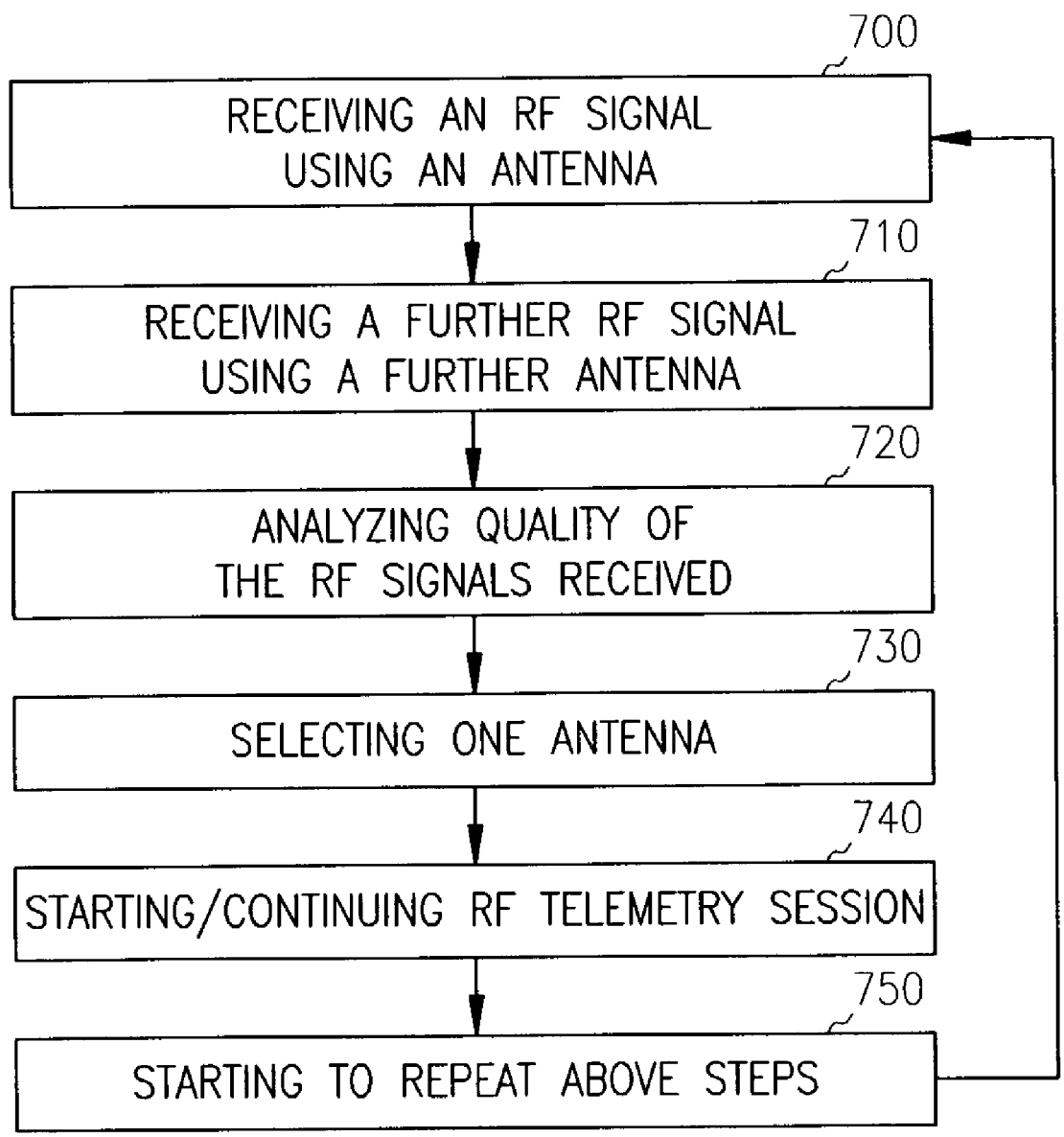
FIG. 7 is a flow chart illustrating one embodiment of a method corresponding to the embodiment of FIG. 5.

FIG. 7 is a flow chart illustrating one embodiment of a method corresponding to the embodiment of FIG. 5. At 700, external telemetry module 122 receives an RF signal through directional antenna 541A. The RF signal is modulated with binary data and transmitted from implanted device 110. In one embodiment, external telemetry module 122 receives the RF signal after it sends out a command causing implanted device 110 to operate in the telemetry testing mode. In this mode, the RF signal is a portion of the RF test signal generated by the RF test signal generator of implanted telemetry module 112. At 710, external telemetry module 122 receives a further RF signal through directional antenna 541B. The further RF signal is substantially similar to the RF signal received at 700 in that both RF signals are generated from the same implanted device 110 at substantially the same distance and modulated with data in substantially the same format. In one mode, the RF signal is a further portion of the RF test signal generated by the RF test signal generator of implanted telemetry module 112. In one embodiment, At 720, signal analyzer 672 analyzes signal quality of both the RF signals received at 700 and 710. In one embodiment, signal analyzer 672 examines data integrity of each of the received RF signals by performing error-checking in accordance with a predetermined protocol. In an additional embodiment, signal analyzer 672 measures the amplitude of each of the received RF signals. At 730, antenna selector 674 selects one of directional antennas 541A and 541B based on an outcome of 720. In one embodiment, antenna selector 674 selects one of directional antennas 541A and 541B that provides a satisfactory data integrity according to a predetermined data integrity standard. In an additional embodiment, when directional antennas 541A and 541B both provide a satisfactory data integrity, antenna selector 674 selects one of directional antennas 541A and 541B providing a higher received RF signal strength. Once an antenna is selected, antenna selector 674 sends the antenna selection control signal to switching circuit 650 to electrically connect one of directional antennas 541A and 541B to transceiver 660, thereby establishing RF telemetry link 190. At 740, if an RF session has not already been started, controller 670 issues a signal to start an RF telemetry session between external device 120 and implanted device 110. If the RF session has been started, it is continued with the directional antenna just selected at 730.

In one embodiment, the RF telemetry session is started during an operation for implanting implanted device 110 into body 101. The RF telemetry session allows external device 120 to monitor a patient's physiological conditions and/or an operational status of implanted device 110 and set parameters for a desired performance of implanted device 110. In an alternative embodiment, the RF telemetry session is started during a postoperative patient examination. The RF telemetry session allows external device 120 to monitor the patient's physiological conditions and/or the operational status of implanted device 110 and, if necessary, adjust parameters for the desired performance of implanted device 110.

In one embodiment, after the RF telemetry session is started at 740, controller 670 starts to repeat steps 700–740, at 750, on a predetermined periodic basis during the RF telemetry session. In another embodiment, after the RF telemetry session is started at 740, signal analyzer 672 monitors the quality of the RF signal on a continuous or periodic basis. At 750, controller 670 starts to repeat steps 700–740 whenever signal analyzer 672 determines that the quality of the RF signal is no longer satisfactory during the RF telemetry session. In one embodiment, steps 700–740 are repeated while the RF telemetry operation is ongoing without significant interruptions to the RF telemetry session. In one embodiment, external device 120 sends a command to implanted device 110 to start to repeat steps 700–740 by causing implanted device to operate in the telemetry testing mode. In this embodiment, the RF telemetry operation is interrupted at least for the period during which implanted device 110 operates in the telemetry testing mode. At the end of each repetition of steps 700–740, if a different directional antenna is selected, the telemetry session continues with the different directional antenna. This ensures that RF telemetry link 190 remains functional throughout the RF telemetry session, even when, for example, implanted device 110 changes position because the patient carrying it moves. The RF telemetry session concludes when all the data transmissions for the session are completed or stopped by an unintended interruption.

Figure 8:
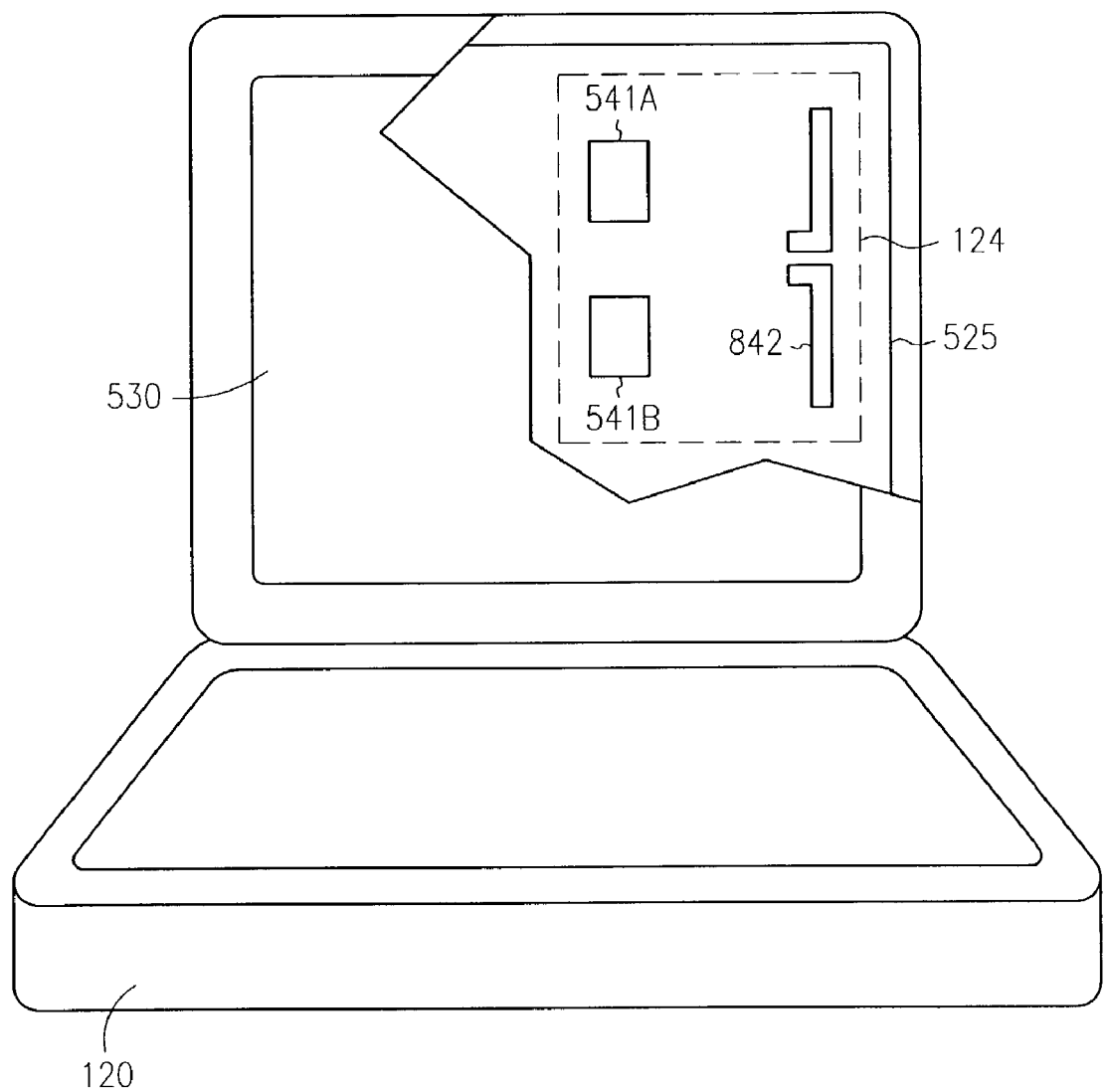
FIG. 8 is a structural diagram illustrating one embodiment of an external device having one non-directional antenna and multiple directional antennas.

FIG. 8 is a structural diagram illustrating one embodiment of an external device having one non-directional antenna and a plurality of directional antennas. External device 120 includes substantially the same structural components, arranged in substantially the same way, as in the embodiment of FIG. 5. In addition, antenna system 124 has a non-directional antenna 842. In one embodiment, as illustrated in FIG. 5, antenna system 124 has directional antennas 541A and 541B and non-directional antenna 842. In one embodiment, non-directional antenna 842 is a single planar dipole antenna. In another embodiment, non-directional antenna 842 is a single planar monopole antenna. In one embodiment, directional antennas 541A and 541B and non-directional antenna 842 are all printed on printed circuit board 525. Size of the dipole or monopole depends on the permittivity of printed circuit board 525. In one embodiment, the printed dipole or monopole is about four to eight centimeters in length. When display screen 530 is positioned about perpendicular to the floor, non-directional antenna 842 is substantially non-directional on a plane parallel to the floor. In another embodiment, non-directional antenna is a loop antenna. In one embodiment, the loop antenna is formed with wire and placed within external device 120, with the plane of the loop being parallel to the base of external device 120. In another embodiment, the loop antenna is printed on a printed circuit board within external device 120 and parallel to the base of external device 120.

In one embodiment, non-directional antenna 842 is non-directional on a plane parallel to a floor on which clinical facilities are established for the user to see patients and perform medical examinations. Directional antennas 541A and 541B are each directional on the same plane on which non-directional antenna 842 is non-directional.

Figure 9:
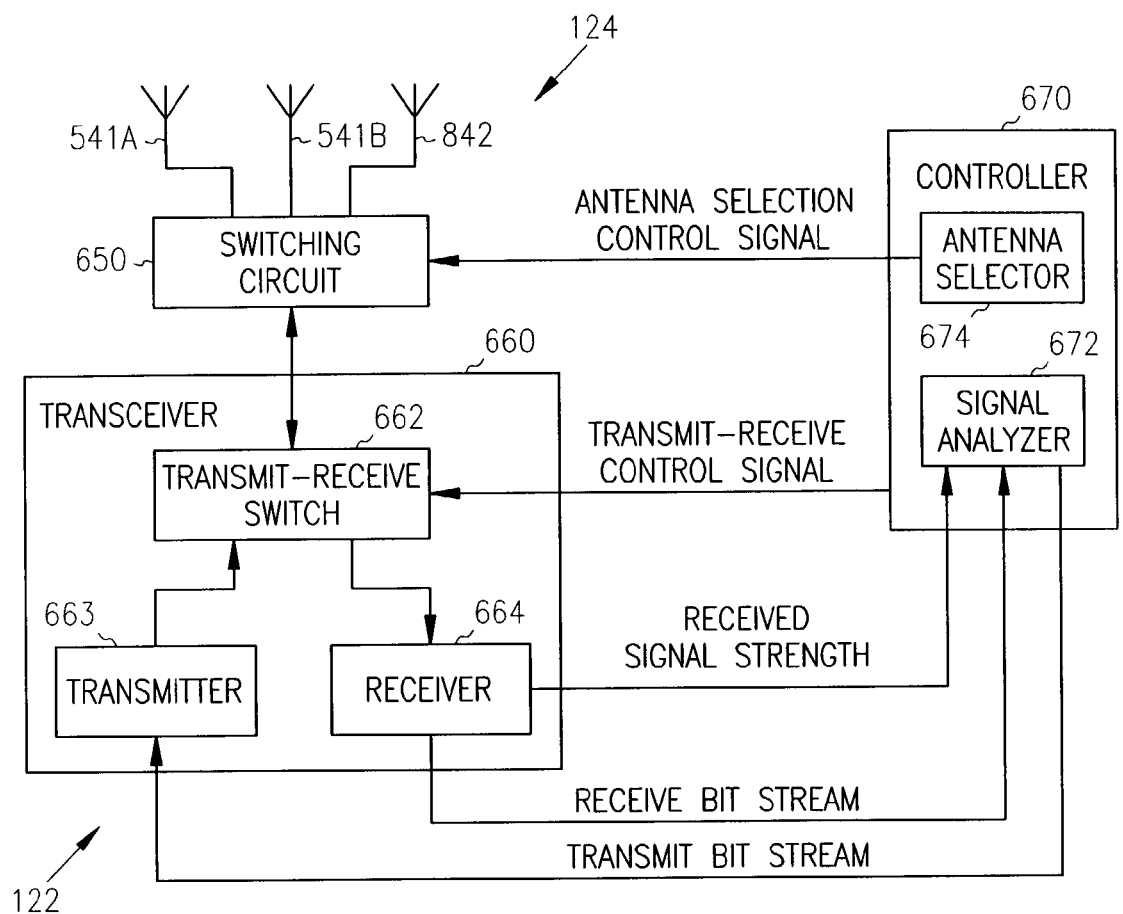
FIG. 9 is a schematic/block diagram illustrating one embodiment of a circuit corresponding to the embodiment of FIG. 8.

FIG. 9 is a schematic/block diagram illustrating one embodiment of a circuit corresponding to the embodiment of FIG. 8. The circuit has substantially the same functional blocks as in the embodiment of FIG. 6. In addition, antenna system 124 has non-directional antenna 842. Each functional block in FIG. 9 has substantially the same type of circuitry as its corresponding functional block in FIG. 6, but modified to accommodate the additional antenna.

Figure 10:
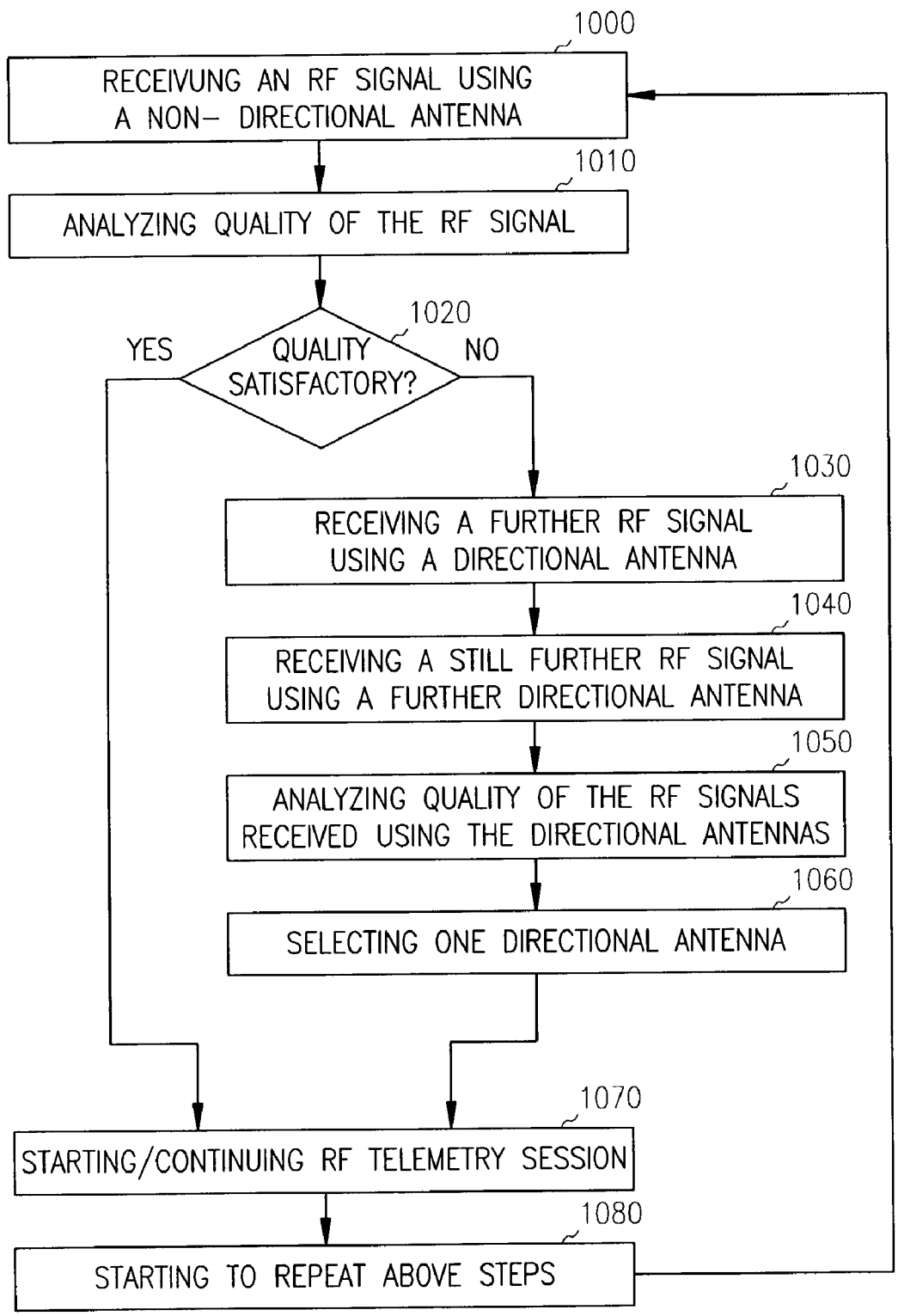
FIG. 10 is a flow chart illustrating one embodiment of a method corresponding to the embodiment of FIG. 8.

FIG. 10 is a flow chart illustrating one embodiment of a method corresponding to the embodiment of FIG. 8. At 1000, external telemetry module 122 receives an RF signal through non-directional antenna 842. The RF signal is modulated with binary data and transmitted from implanted device 110. In one embodiment, external telemetry module 122 receives the RF signal after it sends out a command causing implanted device 110 to operate in the telemetry testing mode. In this mode, the RF signal is a portion of the RF test signal generated by the RF test signal generator of implanted telemetry module 112. At 1010, signal analyzer 672 analyzes quality of the RF signal received at 1000. In one embodiment, signal analyzer 672 examines data integrity of the received RF signal by performing error-checking in accordance with a predetermined protocol. If the quality of the RF signal is found satisfactory under the predetermined protocol at 1020, controller 670 issues a signal to start an RF telemetry session between external device 120 and implanted device 110 using non-directional antenna 842. If the quality of the RF signal is found unsatisfactory at 1020, controller 670 issues a signal to switch to a directional antenna to receive further RF signals.

At 1030, external telemetry module 122 receives a further RF signal through directional antenna 541A. The further RF signal is substantially similar to the RF signal received at 1000 in that both RF signals are generated from the same implanted device 110 at substantially the same distance and modulated with data in substantially the same format. In one mode, the RF signal is a further portion of the RF test signal generated by the RF test signal generator of implanted telemetry module 112. At 1040, external telemetry module 122 receives a still further RF signal through directional antenna 541B. The still further RF signal is also substantially similar to the RF signal received at 1000. In one mode, the RF signal is a still further portion of the RF test signal generated by the RF test signal generator of implanted telemetry module 112. At 1050, signal analyzer 672 analyzes signal quality of both the further and still further RF signals received at 1030 and 1040. In one embodiment, signal analyzer 672 examines data integrity of each of the received RF signals by performing error-checking in accordance with the predetermined protocol. In an additional embodiment, signal analyzer 672 measures the amplitude of each of the received RF signals. At 1060, antenna selector 674 selects one of directional antennas 541A and 541B based on an outcome of analyzing the signal quality of the RF signal at 1050. In one embodiment, antenna selector 674 selects one of directional antennas 541A and 541B that provides a satisfactory data integrity according to the predetermined standard. In an additional embodiment, when directional antennas 541A and 541B each provide a satisfactory data integrity, antenna selector 674 selects one of directional antennas 541A and 541B providing a higher received RF signal strength. Once a directional antenna is selected, antenna selector 674 sends the antenna selection control signal to switching circuit 650 to electrically connect one of the directional antennas 541A and 541B to transceiver 660, thereby establishing RF telemetry link 190. At 1070, if an RF telemetry session has not been started, controller 670 issues a signal to start an RF telemetry session between external device 120 and implanted device 110. If the RF session has been started, it is continued with the antenna just selected at 1020 or 1060.

In one embodiment, after the RF telemetry session is started at 1070, controller 670 starts to repeat steps 1000–1070, at 1080, on a predetermined periodic basis during the RF telemetry session. In another embodiment, after the RF telemetry session is started at 1070, signal analyzer 672 monitors the quality of the RF signal on a continuous or periodic basis. At 1080, controller 670 starts to repeat steps 1000–1070 whenever signal analyzer 672 determines that the quality of the RF signal is no longer satisfactory during the RF telemetry session. In one embodiment, steps 1000–1070 are repeated while the RF telemetry operation is ongoing without significant interruptions to the RF telemetry session. In one embodiment, external device 120 sends a command to implanted device 110 to start to repeat steps 1000–1070 by causing implanted device to operate in the telemetry testing mode. In this embodiment, the RF telemetry operation is interrupted at least for the period during which implanted device 110 operates in the telemetry testing mode. At the end of each repetition of steps 1000–1070, if a different directional antenna is selected, the telemetry session continues with the different directional antenna. This ensures that RF telemetry link 190 remains functional throughout the RF telemetry session, even when, for example, implanted device 110 changes position because the patient carrying it moves. The RF telemetry session concludes when all the data transmissions for the session are completed or stopped by an unintended interruption.

Figure 11:
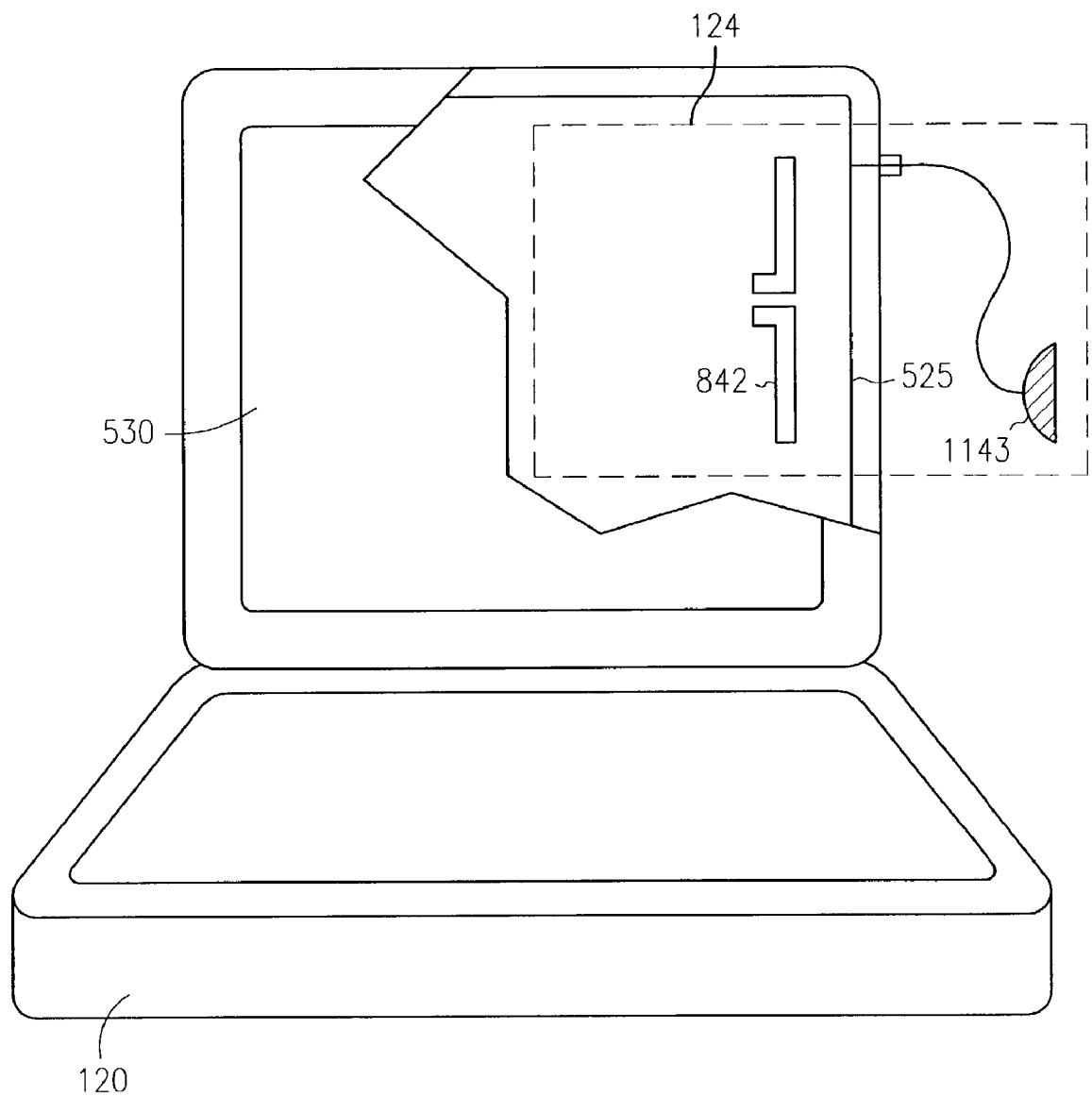
FIG. 11 is a structural diagram illustrating one embodiment of an external device having one non-directional antenna and one directional antenna.

FIG. 11 is a structural diagram illustrating one embodiment of an external device having one non-directional antenna and one directional antenna. External device 120 has substantially the same structural components as in the embodiment of FIG. 5 except that antenna system 124 has non-directional antenna 842 and a directional antenna 1143. In one embodiment, directional antenna 1143 is a hand-held device connected to external device 120 using a cable. In one embodiment, directional antenna 1143 is a parabolic reflector (dish) antenna. In another embodiment, directional antenna 1143 is a planar patch antenna discussed above with reference to FIG. 4. In yet another embodiment, directional antenna 1143 is a slot antenna discussed above with reference to FIG. 4. A user controls the forward direction of directional antenna 1143 by manually aiming directional antenna 1143 to implanted device 110. In one embodiment, the user may place directional antenna 1143 on the patient over implanted device 110. In one further embodiment, directional antenna 1143 is a detachable antenna connected to external device 120 using a cable with a detachable connector. Non-directional antenna 842 is used when directional antenna 1143 is not connected to external device 120. Whenever directional antenna 1143 is connected to external device 120, non-directional antenna 842 is not used. Embodiments using hand-held directional antenna 1143 are suitable, and may be necessary, when RF telemetry link 190 is to be established in a noisy environment where the embodiments described above do not allow the user to establish an RF telemetry link successfully or easily. For example, a postoperative examination of a patient carrying implanted device 110 may occur in a busy clinic where multiple patients wearing similar implantable devices are examined simultaneously in the same room. The busy clinic may also include electronic devices radiating electromagnetic energy, such as MRI machines and cellular phones. This necessitates a high directionality for antenna system 124 that would require a complicated and expensive circuit having a large number of antennas each having a very narrow beamwidth. Under such circumstances, hand-held directional antenna 1143 provides an inexpensive solution. When hand-held directional antenna 1143 is placed on the patient over implanted device 110, or otherwise placed near implanted device 110, RF telemetry link 190 has a high S/N because of the high signal strength associated with the short transmission distance, as compared to the S/N associated with non-directional antenna 842. Thus, hand-held directional antenna 1143 need not have a very narrow beamwidth. In this embodiment, non-directional antenna 842 eliminates the need of manual aiming when the environment does not necessitate the use of a directional antenna.

Figure 12:
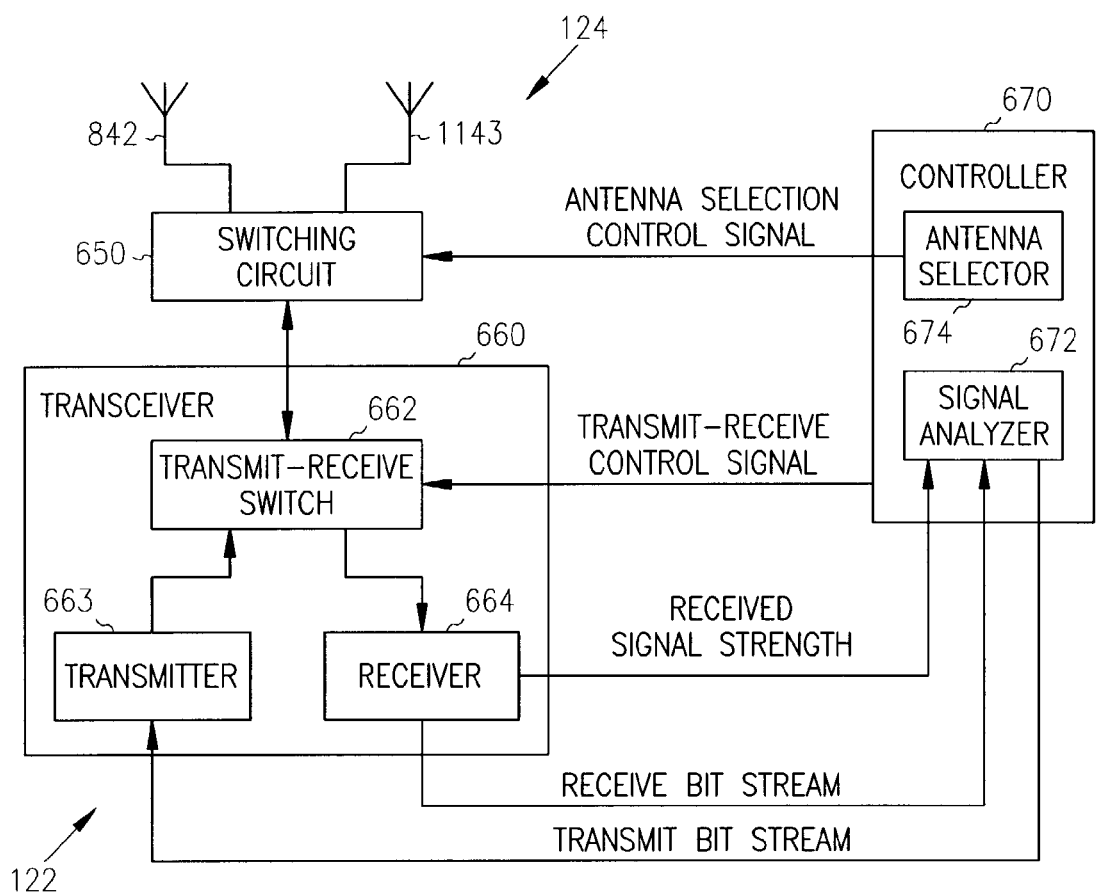
FIG. 12 is a schematic/block diagram illustrating one embodiment of a circuit corresponding to the embodiment of FIG. 11.

FIG. 12 is a schematic/block diagram illustrating one embodiment of a circuit corresponding to the embodiment of FIG. 11. The circuit has substantially the same functional blocks as in the embodiment of FIG. 6, except that antenna system 124 has non-directional antenna 842 and hand-held directional antenna 1143.

Figure 13:
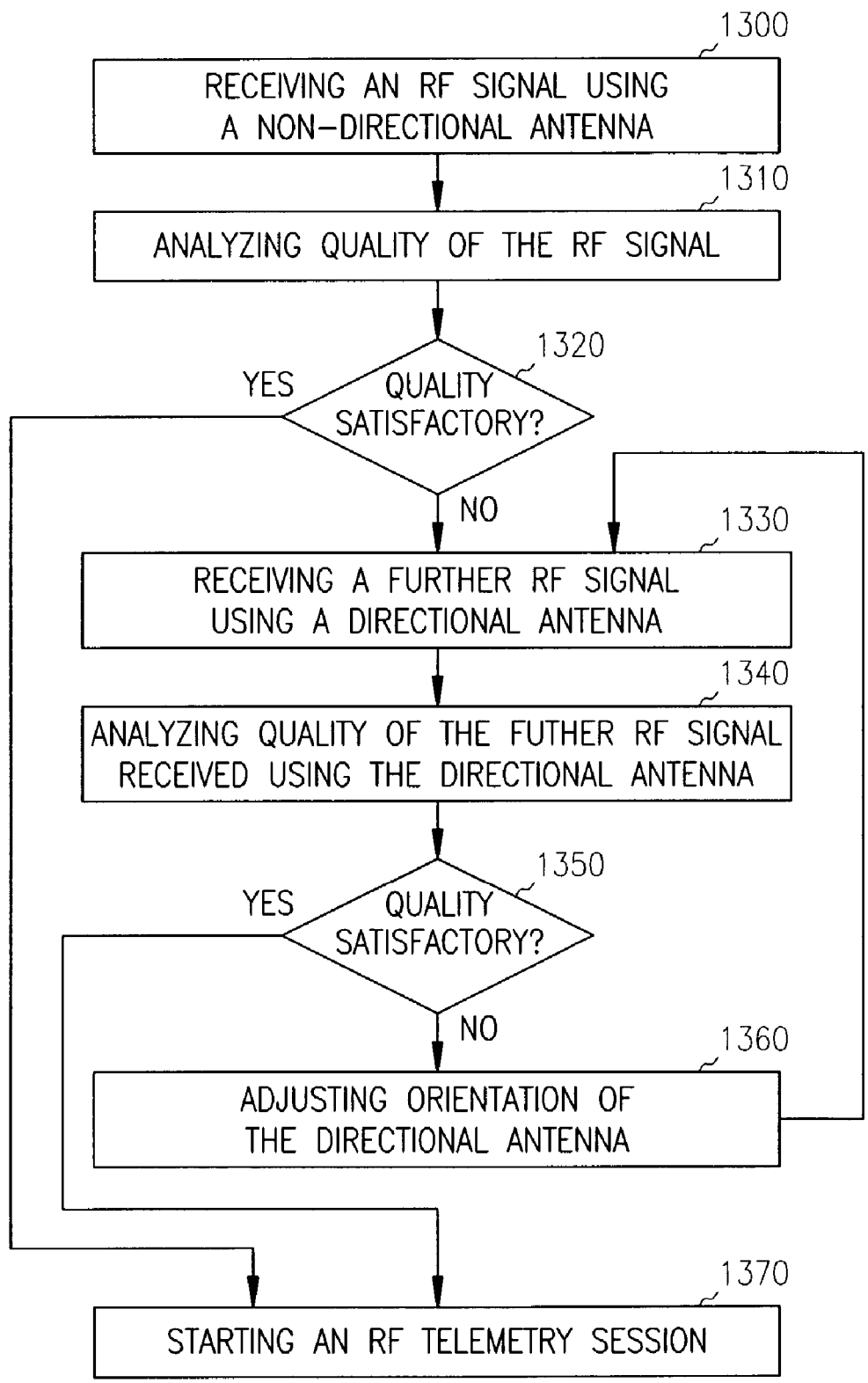
FIG. 13 is a flow chart illustrating one embodiment of a method corresponding to the embodiment of FIG. 11.

FIG. 13 is a flow chart illustrating one embodiment of a method corresponding to the embodiment of FIG. 11. At 1300, external telemetry module 122 receives an RF signal through non-directional antenna 842. The RF signal is modulated with binary data and transmitted from implanted device 110. In one embodiment, external telemetry module 122 receives the RF signal after it sends out a command causing implanted device 110 to operate in the telemetry testing mode. In this mode, the RF signal is the RF test signal generated by the RF test signal generator of implanted telemetry module 112. At 1310, signal analyzer 672 analyzes signal quality of the RF signal received at 1300. In one embodiment, signal analyzer 672 examines data integrity of the received RF signal by performing error-checking in accordance with a predetermined protocol. If the quality of the RF signal is found satisfactory under the predetermined protocol at 1320, controller 670 issues a signal at 1370 to start an RF telemetry session between external device 120 and implanted device 110. If the quality of the RF signal is found unsatisfactory at 1320, further RF signals will be received through directional antenna 1143.

At 1330, external telemetry module 122 receives a further RF signal through directional antenna 1143. The further RF signal is substantially similar to the RF signal received at 1300 in that both RF signals are generated from the same implanted device and modulated with data in substantially the same format. In one embodiment, where directional antenna 1143 is a detachable antenna, directional antenna 1143 is connected to external device 120 before external telemetry module 122 receives the further RF signal at 1330. At 1340, signal analyzer 672 analyzes signal quality of the further RF signal received at 1330. In one embodiment, signal analyzer 672 examines data integrity of the further RF signal by performing error-checking in accordance with a predetermined protocol. If the quality of the RF signal is found satisfactory under the predetermined protocol at 1350, controller 670 issues a signal at 1370 to start an RF telemetry session between external device 120 and implanted device 110. If the quality of the RF signal is found unsatisfactory at 1350, the user adjusts the orientation of directional antenna 1143 by re-aiming it to implanted device 110. Steps

1330–1360 are repeated until the quality of the RF signal is found satisfactory at 1350. At 1370, controller 670 issues a signal to start an RF telemetry session between external device 120 and implanted device 110.

In an alternative embodiment, where directional antenna 1143 is a detachable antenna, the user starts to use directional antenna 1143 by connecting it to external device 120 at any time. In one embodiment, the user starts to use directional antenna 1143 upon his judgment on the presence and magnitude of the interference. In one specific embodiment, the user makes the judgment based on observations of cardiac signals displayed by external device 120. In another embodiment, the user starts to use directional antenna 1143 when external device 120 indicates an unacceptable amount or rate of data transmission errors. In one specific embodiment, implanted device 110 and external device 120 each include error-checking modules to ensure the integrity of data transmitted in both directions via RF telemetry link 190. When the number and/or frequency of errors detected exceed a predetermined threshold, external device 120 provides a signal to the user to replace non-directional antenna 842 with directional antenna 1143 if non-directional antenna 842 is being used, or to reposition directional antenna 1143 if it is being used.

Figure 14:
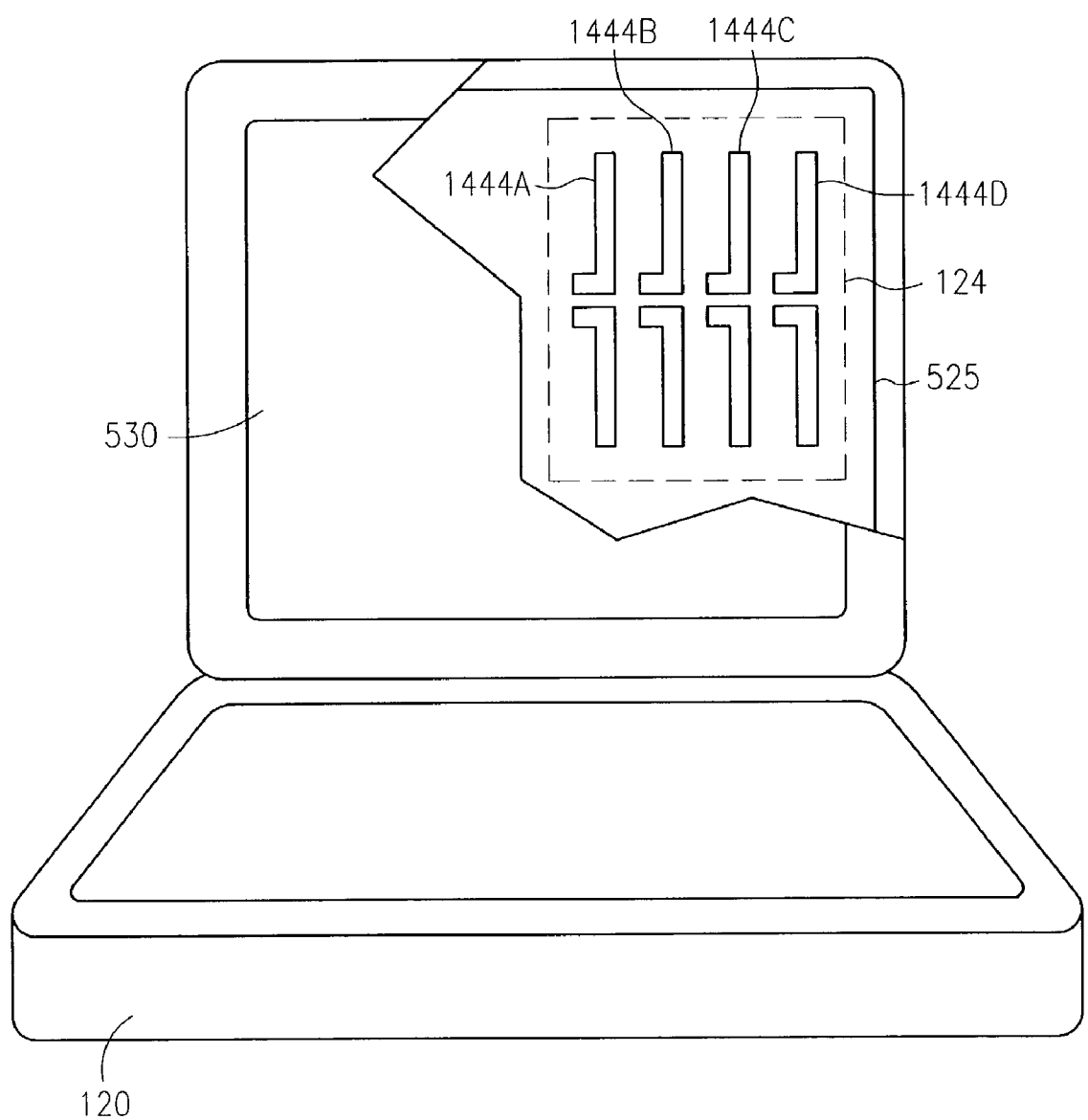
FIG. 14 is a structural diagram illustrating one embodiment of an external device having a phased-array directional antenna.

FIG. 14 is a structural diagram illustrating one embodiment of an external device having a phased-array directional antenna. External device 120 has substantially the same structural components, arranged in substantially the same way, as in the embodiment of FIG. 5, except that antenna system 124 has a directional antenna 1444, which is the phased-array directional antenna. Directional antenna 1444 includes two or more antennas acting its antenna elements. In one embodiment, the antenna elements are each a planar dipole antenna. In one further embodiment, directional antenna 1444 is printed on printed circuit board 525. Size of each of the dipole antennas depends on the permittivity of printed circuit board 525. In one embodiment, each of the dipole antennas is about four to eight centimeters in length. An effective forward direction, or effective orientation of directional antenna 1444 and also antenna system 124, is controlled by electronically driving the antenna elements out of phase. In one embodiment, the antenna elements are driven out of phase by introducing a weighting factor into an RF signal transmitted or received through each of the antenna elements. Each weight factor is a vector including an amplitude and a phase angle. The weighting factors are multiplied with the RF signals to modify a phase angle of each RF signal. The effective orientation of antenna 1444 is steered by controlling one or more phase angles of the RF signals transmitted or received through the antenna elements. In an alternative embodiment, the antenna elements are driven out of phase by introducing different transmission delays to the antenna elements. Because RF signals transmitted or received through the plurality of antenna elements each has a phase angle depending on the conduction delay, the effective orientation of antenna 1444 can be steered by adjusting the transmission delays. In one embodiment, the plurality of antenna elements are each connected to a delay line. In one embodiment, each delay line is a conductive path being a wire or a metal path on printed circuit board 525. The transmission delay of each delay line is proportional to its length. Thus, the effective orientation of antenna 1444 can be steered by adjusting how the delay lines and the antenna elements are paired.

In one embodiment, as illustrated in FIG. 14, directional antenna 1444 has, by way of example, but not by way of limitation, four antenna elements 1444A–D. In an alternative embodiment, directional antenna 1444 has two antenna elements. In another alternative embodiment, directional antenna 1444 has more than four antenna elements. The number of antenna elements included in directional antenna 1444 is chosen based on a compromise among factors including cost, circuit complexity, and desirable degree of directionality.

Figure 15:
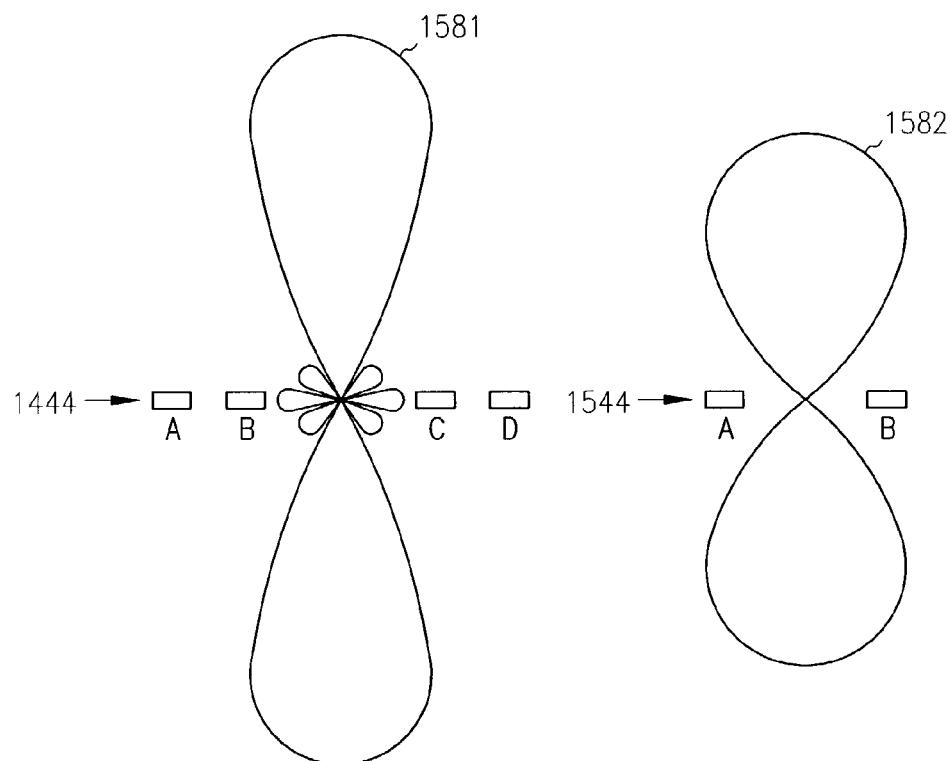
FIG. 15 is an illustration of radiation patterns of a four-element phased array directional antenna and a two-element phased array directional antenna.

FIG. 15 is an illustration of radiation patterns of a four-element phased array directional antenna and a two-element phased array directional antenna. A radiation pattern 1581 illustrates an example of a directionality characteristic of directional antenna 1444, when antenna elements 1444A–D are not driven out of phase, in a plane perpendicular to circuit board 525 and hence about parallel to the floor. In one embodiment, radiation pattern 1581 is obtained by applying equal weighting factors to all of antenna elements 1444A–D. In an alternative embodiment, radiation pattern 1581 is obtained by introducing the same transmission delay to each of antenna elements 1444A–D.

A directional antenna 1544 is substantially the same as directional antenna 1444 except that antenna 1544 has two, instead of four, antenna elements 1544A and 1544B. A radiation pattern 1582 illustrates an example of a directional characteristic of directional antenna 1544, when antenna elements 1544A and 1544B are not driven out of phase, in the plane perpendicular to circuit board 525, and hence about parallel to the floor during an RF telemetry session. As illustrated by radiation patterns 1581 and 1582, having more antenna elements provides for a narrower beamwidth centered at each effective orientation, thereby enhancing the advantage of the directional antenna in reducing chance of interference and increasing the communication range in the direction aligned with the effective orientation of the directional antenna. On the other hand, fewer antenna elements require a simpler electronic steering system.

Figure 16:
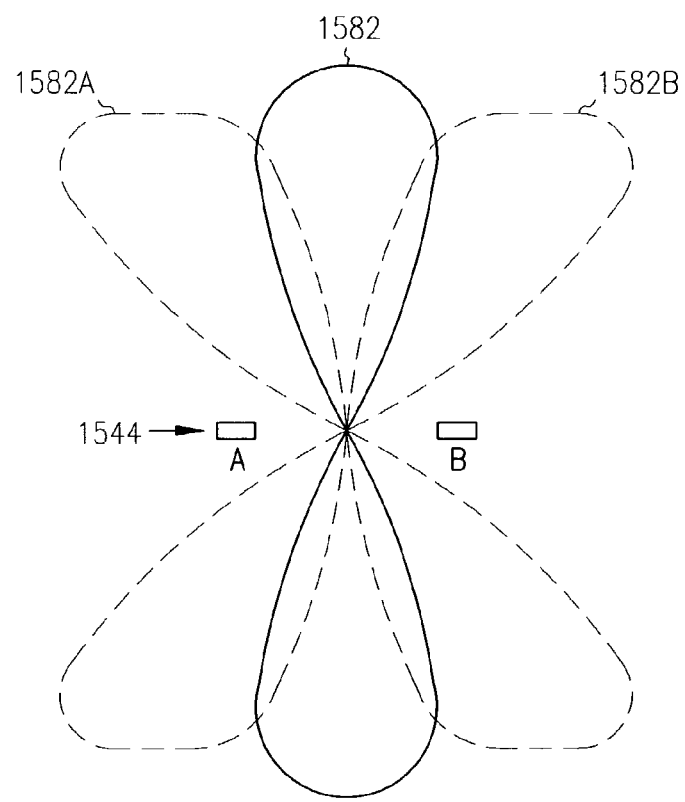
FIG. 16 is an illustration of radiation patterns of a two-element phased array directional antenna when driven out of phase.

FIG. 16 is an illustration of radiation patterns of a two-element phased array directional antenna when driven out of phase. Same as in FIG. 15, directional antenna 1544 has radiation pattern 1582 when it is not driven out of phase. Radiation patterns 1582A and 1582B illustrate the effect of driving directional antenna 1544 out of phase. The effective orientation of directional antenna 1544 is the direction at which directional antenna 1544 has the highest gain. Thus, radiation patterns 1582, 1582A, and 1582B are each related to a different effective orientation of directional antenna 1544. In one embodiment, directional antenna 1544 is driven out of phase when the two weighting factors introduced to antenna elements 1544A and 1544B have at least a relatively different phase angle. The effective orientation of directional antenna 1544 is steered by adjusting at least the relative phase difference between the two weighting factors. In an alternative embodiment, directional antenna 1544 is driven out of phase when antenna elements 1544A and 1544B are tuned to introduce different phase angles to the RF signals transmitted or received through antenna elements 1544A and 1544B.

Directional antenna 1444 or 1544 allows electronic alignment between external antenna system 124 and implanted antenna system 114 to establish RF telemetry link 190. This eliminates the need for physically positioning external device 120. As compared to an antenna system having two or more planar patch or slot directional antennas, a phased-array directional antenna is potentially more suitable when relatively fine directionality is required or desired. In other words, a phased-array directional antenna is suitable for establishing RF telemetry link 190 in a clinical environment where narrow antenna beamwidth is necessary or desired.

Figure 17:
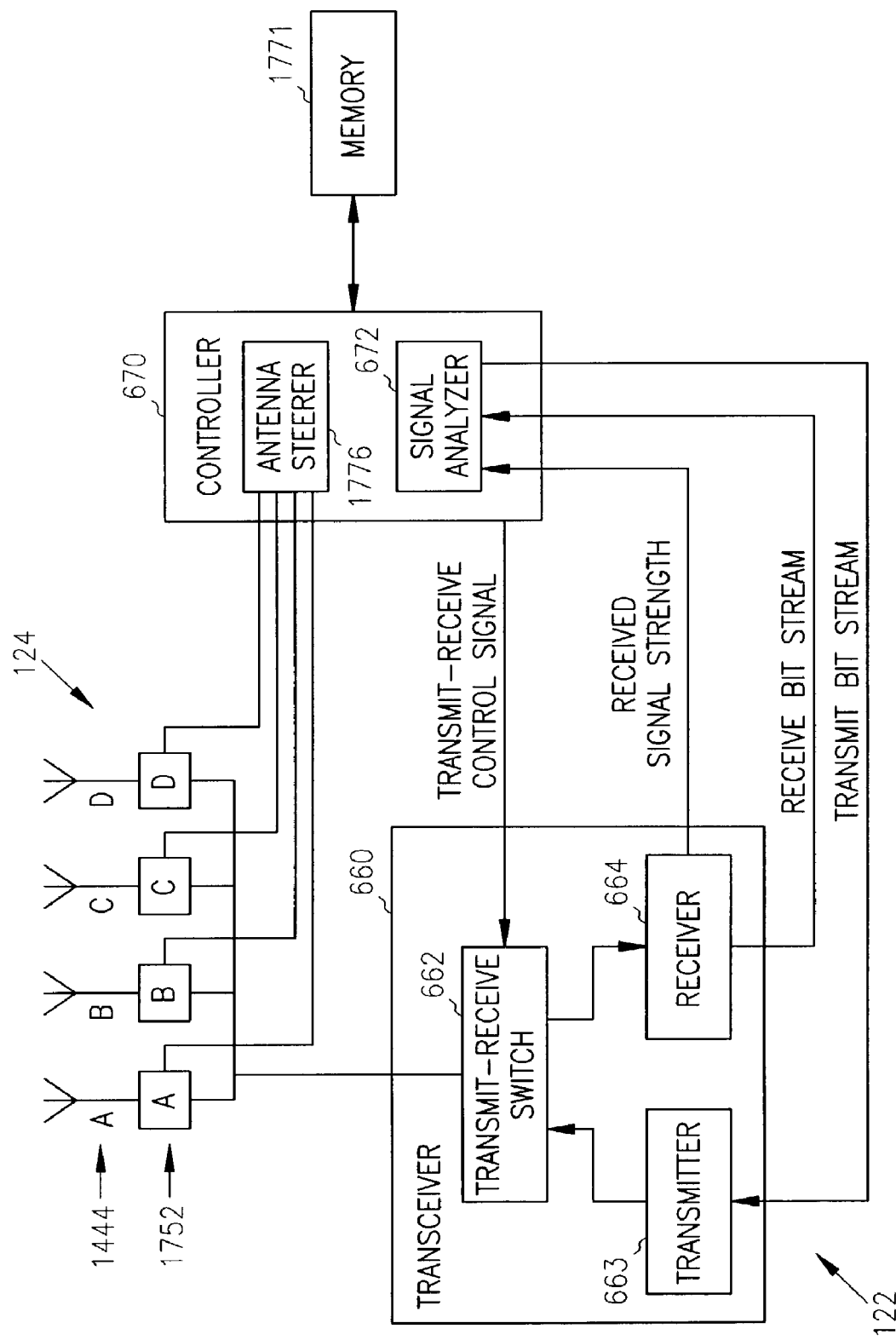
FIG. 17 is a schematic/block diagram illustrating one embodiment of a circuit corresponding to the embodiment of FIG. 14.

FIG. 17 is a schematic/block diagram illustrating one embodiment of a circuit corresponding to the embodiment of FIG. 14. The circuit constitutes portions of external telemetry module 122 and an antenna system 124. In one embodiment, antenna system 124 has, by way of example, but not by way of limitation, a phased-array antenna 1444 having antenna elements 1444A–D. External telemetry module 122 includes a transceiver 660, a controller 670, and an antenna interface circuit 1752. Transceiver 660 is substantially the same as, or substantially similar to, the same element as in the embodiment of FIG. 6.

Controller 670 controls whether transceiver 660 transmits or receives RF signals and includes a signal analyzer 672 and an antenna steerer 1776. The signal analyzer analyzes signal quality of RF signals received at a plurality of effective orientations of directional antenna 1444. In one embodiment, signal analyzer 672 measures the amplitude of the RF signal received at each of the plurality of effective orientations. In a further embodiment, signal analyzer 672 examines integrity of the data recovered by transceiver 660 and generates a data integrity indicator. Antenna steerer 1776 is a directionality controller of antenna system 124. In the embodiment of FIG. 17, Antenna steerer 1776 controls the directionality of antenna system 124 by determining the effective orientation associated with the best signal quality, steering directional antenna 1444 to that effective orientation, and locking directional antenna 1444 in that effective orientation. In one embodiment, antenna system 124 is coupled to transceiver 660 through antenna interface circuit 1752, which is an antenna orientation circuit allowing effectively orientation of directional antenna 1444. In one embodiment, antenna interface circuit 1752 includes individual interface circuits 1752A–D respectively connected to antenna elements 1444A–D. In one embodiment, interface circuits 1752A–D are multipliers allowing the weighting factors to be multiplied with RF signals received through antenna elements 1444A–D, respectively. In one embodiment, a table containing the weighting factors defining the plurality of effective orientations of directional antenna 1444 is stored in a memory 1771. Antenna steerer 1776 applies the weighting factors to sweep through the plurality of effective orientations to test directional antenna 1444 at each of the plurality of effective orientations. In an alternative embodiment, interface circuits 1752A–D are delay elements each having an adjustable transmission delay. In one embodiment, delay elements 1752A–D each include wires or other metal paths of different length. The transmission delay is adjusted by selecting one of the wires or other metal paths to connect to the corresponding antenna element. Antenna steerer 1776 controls the transmission delay of each of delay elements 1752A–D to result in the plurality of effective orientations at which directional antenna 1444 will be tested. In one embodiment, a table containing transmission delays defining the plurality of effective orientations is stored in memory 1771. In another embodiment, interface circuit 1752 includes an array of delay lines each associated with a different transmission delay. The number of the delay lines in the array is equal to or more than the number of antenna elements in antenna 1444. Antenna steerer 1776 includes a delay line selector that selects delay lines from the array of delay lines and selectively couples each of the selected delay lines between one of antenna elements 1444A–D and transceiver 660. Delay elements 1752A–D represent these selected delay lines. Antenna elements 1444A–D and the array of delay lines are connected in a plurality of combinations to result in the plurality of effective orientations at which directional antenna 1444 will be tested.

Figure 18:
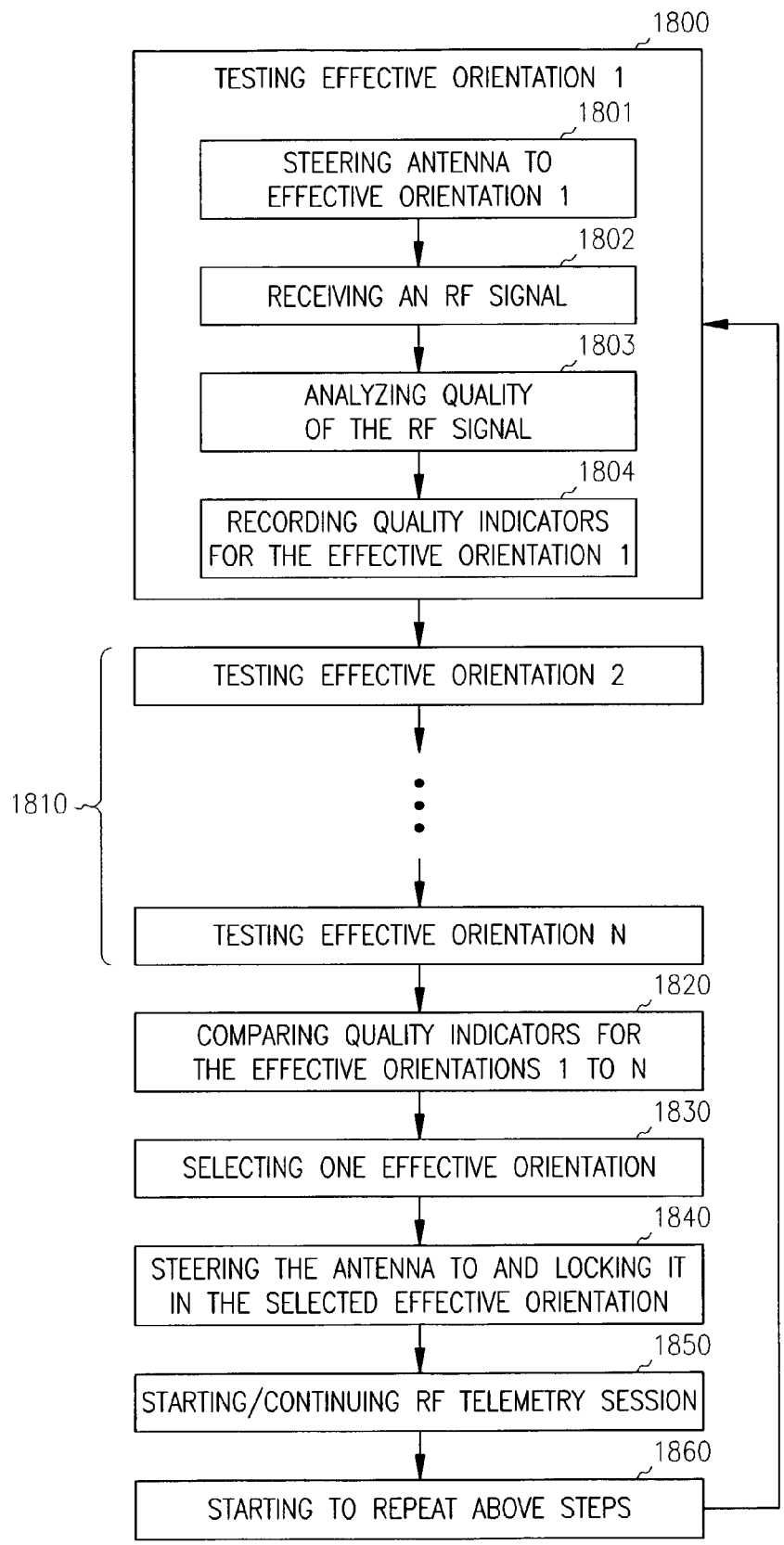
FIG. 18 is a flow chart illustrating one embodiment of a method corresponding to the embodiment of FIG. 14.

FIG. 18 is a flow chart illustrating one embodiment of a method corresponding to the embodiment of FIG. 14. Directional antenna 1444 is tested at a predetermined number (N) of effective orientations. The number of effective orientations to be tested depends on the beamwidth of directional antenna 1444 and the total range of directions to be tested. In one embodiment, the predetermined total range of directions is 0°–360°, i.e., the N effective orientations cover a 360° space in one plane. In another embodiment, the total range of directions includes one or more portions of 0°–360°, i.e., the N effective orientations cover one or more less-than-360° spaces in one plane. In one embodiment, the total range of directions is equally divided over the first to Nth effective orientations, resulting in first through Nth spaces. In one specific embodiment, directional antenna 1444 has a constant beamwidth, and N equals approximately 360° divided by that beamwidth (in term of degrees).

At 1800, directional antenna 1444 is tested for a first effective orientation. The first effective orientation is the first of the predetermined number of effective orientations at which directional antenna 1444 will be tested. Testing directional antenna 1444 at the first effective orientation includes at least four steps 1801–1804. At 1801, antenna steerer 1776 electronically steers directional antenna 1444 to a first effective orientation. In one embodiment, directional antenna 1444 is electronically steered by applying the weighting factors to RF signals received through each of antenna elements 1444A–D. In another embodiment, directional antenna 1444 is electronically steered by adjusting the transmission delays associated with antenna elements 1444A–D. At 1802, external telemetry module 122 receives an RF signal through directional antenna 1444. The RF signal is modulated with binary data and transmitted from implanted device 110. In one embodiment, external telemetry module 122 receives the RF signal after it sends out a command causing implanted device 110 to operate in the telemetry testing mode. In this mode, the RF signal is at least a portion of the RF test signal generated by the RF test signal generator of implanted telemetry module 112. At 1803, signal analyzer 672 analyzes signal quality of the RF signal received at 1802. In one embodiment, signal analyzer 672 examines data integrity of the received RF signal by performing error-checking in accordance with a predetermined protocol. In an additional embodiment, signal analyzer 672 measures the amplitude of the received RF signal. At 1804, one or more quality indicators associated with the first effective orientation, as an outcome of analyzing the quality of the RF signal at 1803, are recorded. The recording of the one or more quality indicators associated with the first effective orientation concludes the test of directional antenna 1444 for the first effective orientation.

At 1810, directional antenna 1444 is tested, one at a time, at each of the predetermined number (N) of effective orientations covering a predetermined total range of directions. This includes repeating the test procedure of 1801–1804 for a second through Nth effective orientations. In one embodiment, external telemetry module 122 starts testing the first effective orientation after it sends out a command causing implanted device 110 to operate in the telemetry testing mode. In a further embodiment, implanted device 110 operates in the telemetry testing mode until the Nth effective orientation has been tested. In this mode, the RF signal in each repetition of steps 1801–1804 is a portion of the RF test signal generated by the RF test signal generator of implanted telemetry module 112. As a result, N sets of quality indicators are recorded, corresponding to the N effective orientations. At 1820, antenna steerer 1776 compares among the N sets of quality indicators. In one embodiment, antenna steerer 1776 compares the amplitudes of the RF signals received at the N effective orientations to determine the effective orientation providing the largest RF signal amplitude. In an alternative embodiment, antenna steerer 1776 compares the amplitudes of the RF signals received at the effective orientations at which the data integrity is satisfactory to determine the effective orientation providing the largest RF signal amplitude and a satisfactory data integrity. At 1830, antenna steerer 1776 selects an effective orientation at which an RF telemetry session will be started, based on an outcome of the comparison among the quality indicators at 1820. In one embodiment, antenna steerer 1776 selects the effective orientation providing the largest RF signal amplitude. In another embodiment, antenna steerer 1776 selects an effective orientation providing a satisfactory data integrity. In a further embodiment, antenna steerer 1776 selects the effective orientation providing the largest RF signal amplitude while providing a satisfactory data integrity. After the effective orientation is selected at 1830, antenna steerer 1776 electronically steers directional antenna 1444 to the selected effective orientation and locks directional antenna 1444 in that effective direction at 1840. At 1850, controller 670 issues a signal to start an RF telemetry session between external device 120 and implanted device 110.

In one embodiment, after the RF telemetry session is started at 1850, controller 672 starts to repeat steps 1800–1850, at 1860, on a predetermined periodic basis during the RF telemetry session. In a further embodiment, at 1860, controller 670 starts to repeat steps 1800–1850 on the predetermined periodic basis with a different set of effective orientations 1 to N that is limited to cover a vicinity of the effective orientation that directional antenna 1444 has been locked into. This enables the effective orientation of directional antenna 1444 to track, for example, the direction of the patient moving within a limited area, such as running on a treadmill. In another embodiment, after the RF telemetry session is started at 1850, signal analyzer 672 monitors the quality of the RF signal on a continuous or periodic basis. At 1860, controller 670 starts to repeat steps 1800–1850 whenever signal analyzer 672 determines that the quality of the RF signal is no longer satisfactory during the RF telemetry session. In one embodiment, steps 1800–1850 are repeated while the RF telemetry operation is ongoing without significant interruptions to the RF telemetry session. In one embodiment, external device 120 sends a command to implanted device 110 to start to repeat steps 1800–1850 by causing implanted device to operate in the telemetry testing mode. In this embodiment, the RF telemetry operation is interrupted at least for the period during which implanted device 110 operates in the telemetry testing mode. At the end of each repetition of steps 1800–1850, if a new effective orientation is selected, directional antenna 1444 is locked in the new effective orientation. This ensures that RF telemetry link 190 remains functional throughout the RF telemetry session, even when, for example, implanted device 110 changes position because the patient carrying it moves. The RF telemetry session concludes when all the data transmissions for the session are completed or stopped by an unintended interruption.

Figure 19:
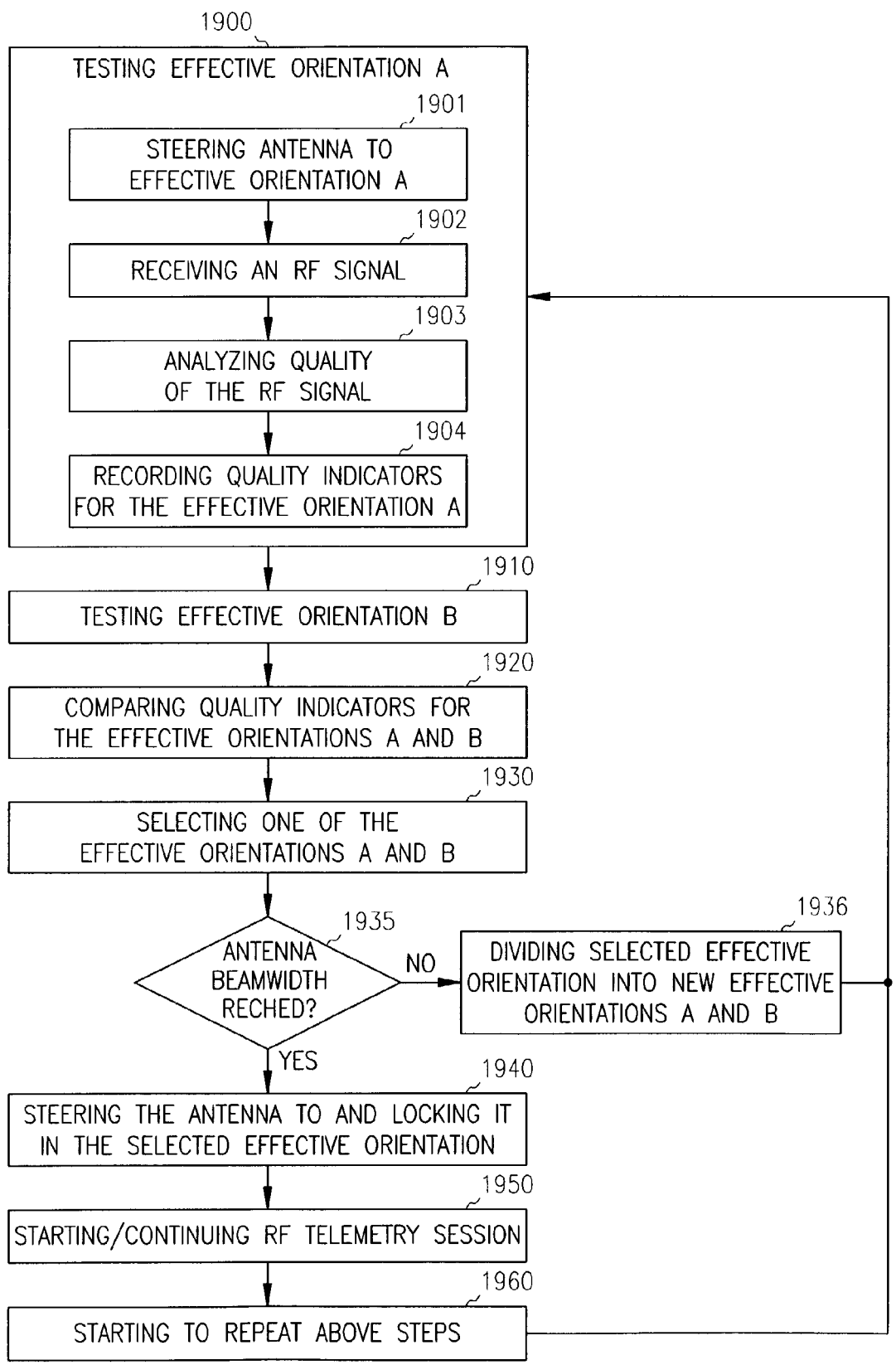
FIG. 19 is a flow chart illustrating another embodiment of the method corresponding to the embodiment of FIG. 14.

FIG. 19 is a flow chart illustrating another embodiment of the method corresponding to the embodiment of FIG. 14. In this embodiment, an operating beamwidth is predetermined for directional antenna 1444. The operating beamwidth applies throughout an RF telemetry session except for periods during which an effective orientation is being tested. The predetermined total range of directions is first divided into two spaces corresponding to effective orientations A and B. In one embodiment, the predetermined total range of directions is first equally divided into two spaces, such that directional antenna 1444 has the same beamwidth to cover each of the effective orientations A and B. Steps 1900, 1910, 1920, and 1930 are substantially the similar to steps 1800, 1810, 1820, and 1830, respectively, expect that directional antenna 1444 is tested for only one effective direction (B) at 1910. As a result, two sets of quality indicators are recorded, corresponding to the effective orientations A and B. At 1920, antenna steerer 1776 compares among the two sets of quality indicators. Step 1920 is substantially similar to step 1820 with N equal to two. At 1930, antenna steerer 1776 selects one of the effective orientations A and B based on an outcome of the comparison among the quality indicators at 1920. The criteria for the selection are substantially similar to the criteria discussed above with respect to step 1830. At 1935, if the selected effective orientation corresponds to a range of directions equal to or narrower than the predetermined operating beamwidth of directional antenna 1444, antenna steerer 1776 electronically steers directional antenna 1444 to the selected effective orientation if it has not already pointed to that direction, and locks directional antenna 1444 in that effective direction at 1940. If the selected effective orientation corresponds to a range of directions wider than the predetermined operating beamwidth of directional antenna 1444, the range of directions covered by the selected effective orientation is further divided into a new set of effective orientations A and B at 1936. In one embodiment, the range of directions covered by the selected effective orientation is equally divided into two spaces, such that directional antenna 1444 has the same beamwidth to cover each of the new set of effective orientations A and B. Steps 1900–1935 are repeated until the selected effective orientation corresponds to a range of directions equal to or narrower than the predetermined operating beamwidth of directional antenna 1444. At 1950, if an RF session has not been started, controller 670 issues a signal to start an RF telemetry session between external device 120 and implanted device 110. If the RF session has been started, it is continued with directional antenna being locked on the latest selected effective orientation.

In one embodiment, after the RF telemetry session is started at 1950, controller 670 starts to repeat steps 1900–1950, at 1960, on a predetermined periodic basis during the RF telemetry session. In a further embodiment, at 1960, controller 670 starts to repeat steps 1900–1950 on the predetermined periodic basis with the effective orientations A and B being limited to a vicinity of the effective orientation that directional antenna 1444 has been locked into. This enables the effective orientation of directional antenna 1444 to track, for example, the direction of the patient moving within a limited area, such as running on a treadmill. In another embodiment, after the RF telemetry session is started at 1950, signal analyzer 672 monitors the quality of the RF signal on a continuous or periodic basis. At 1960, controller 670 starts to repeat steps 1900–1950 whenever signal analyzer 672 determines that the quality of the RF signal is no longer satisfactory during the RF telemetry session. In one embodiment, steps 1900–1950 are repeated while the RF telemetry operation is ongoing without significant interruptions to the RF telemetry session. In one embodiment, external device 120 sends a command to implanted device 110 to start to repeat steps 1900–1950 by causing implanted device to operate in the telemetry testing mode. In this embodiment, the RF telemetry operation is interrupted at least for the period during which implanted device 110 operates in the telemetry testing mode. At the end of each repetition of steps 1900–1950, if a new effective orientation is selected, directional antenna 1444 is locked in the new effective orientation. This ensures that RF telemetry link 190 remains functional throughout the RF telemetry session, even when, for example, implanted device 110 changes position because the patient carrying it moves.

If dividing the predetermined total range of directions by two results in two spaces each being wider than the maximum beamwidth of directional antenna 1444, portions of the methods of FIG. 18 and FIG. 19 are to be combined. The predetermined total range of directions is first divided by N to result in N equal spaces each being no wider than the maximum beamwidth of directional antenna 1444. One of the N equal spaces is selected as the effective orientation by performing 1800–1830 discussed above with reference to FIG. 18. This effective direction then serves as the predetermined total range of directions that is to be divided by two to result in the effective orientations A and B of the method of FIG. 19. Then, the method of FIG. 19 is performed. In one specific embodiment, as an example, the predetermined total range of directions includes a 360° space. Directional antenna 1444 has a maximum beamwidth of 120°. The 360° space is first divided into three 120° spaces, corresponding to the effective orientations 1 to N (N=3) that are tested at 1800–1830. Then, one of the three 120° spaces is selected at 1830. If the operating beamwidth of directional antenna 1444 is predetermined to be narrower than 120°, the selected 120° space is divided into two 60° spaces, corresponding to the effective orientations A and B that are tested by performing 1900–1930. At 1930, one of the two 60° spaces is selected. If the predetermined operating beamwidth of directional antenna 1444 is narrower than 60°, the selected 60° space is divided into two 30° spaces, corresponding to a new set of effective orientations A and B that are tested by repeating 1900–1930. The process proceeds to step 1940 if the operating beamwidth of directional antenna 1444 is predetermined to be at least 30°. In general, this loop of repeated testing and selection (1900–1930) ends when the effective orientation selected at 1930 corresponds to an angular space equal to or narrower than the operating beamwidth of directional antenna 1444.

It is to be understood that the above detailed description is intended to be illustrative, and not restrictive. For example, the implantable device can be any implantable medical device having an active electronic circuit. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system for communicating with an implantable medical device, the system comprising:
   an external device adapted to be communicatively coupled to the implantable medical device via radio-frequency (RF) telemetry and adapted to control operation of the implantable medical device and receive data from the implantable medical device, the external device comprising:
      a transceiver;
      an antenna system comprising at least two antennas each being directional on at least one plane and having a predetermined half-power beamwidth of less than about 180 degrees;
      an antenna interface circuit coupled between the transceiver and the antenna system; and
      a directionality controller coupled to the antenna interface circuit, the directionality controller adapted to control a directionality of the antenna system.

2. The system of claim 1, wherein the implantable medical device comprises at least one of a pacemaker, a cardioverter/defibrillator, a cardiac resynchronization therapy device, and a drug delivery device.

3. The system of claim 2, wherein the external device comprises a programmer adapted to program the implantable medical device.

4. The system of claim 2, wherein the external device comprises a monitor adapted to monitor at least one physiologic signal acquired by the implantable medical device.

5. The system of claim 1, further comprising a signal analyzer coupled to the transceiver and the directionality controller, the signal analyzer adapted to analyze a quality of each of one or more RF signals received by one or more of the at least two antennas, and wherein the directionality controller is adapted to control the directionality of the antenna system based on the quality of the each of the one or more RF signals.

6. The system of claim 5, wherein the signal analyzer comprises a signal strength detector adapted to measure an amplitude of the each of the one or more RF signals.

7. The system of claim 5, wherein the signal analyzer comprises a data integrity detector adapted to determine whether data contained in the each of the one or more RF signals meet predetermined quality criteria.

8. The system of claim 5, wherein the implantable medical device comprises an RF test signal generator to generate the one of more RF signals, upon receiving a command from the external device to cause the implantable medical device to operate in a telemetry testing mode.

9. The system of claim 5, wherein:
   the antenna interface circuit comprises a switching circuit adapted to provide electrical connection between the transceiver and one of the at least two antennas; and
   the directionality controller comprises an antenna selector adapted to control the electrical connection between the transceiver and the at least two antennas based on the quality of the each of the one or more RF signals received by each of the at least two antennas.

10. The system of claim 9, wherein the at least two antennas are each one of a planar patch antenna, a slot antenna, a parabolic reflector antenna, a Uda-Yagi antenna, and a helical antenna.

11. The system of claim 9, wherein the at least two antennas are printed on a printed circuit board housed in the external device.

12. The system of claim 11, wherein each of the at least two antennas is one of a planar patch antenna and a slot antenna.

13. The system of claim 9, wherein the at least two antennas are configured to be antennas having substantially different beamwidths.

14. A system for communicating with an implantable medical device, the system comprising:
   an external device adapted to be communicatively coupled to the implantable medical device via radio-frequency (RF) telemetry and adapted to control operation of the implantable medical device and receive data from the implantable medical device, the external device comprising:
      a transceiver;

an antenna system comprising a first antenna being approximately non-directional on at least one plane and a second antenna being directional on the at least one plane;
an antenna interface circuit coupled between the transceiver and the antenna system; and
a directionality controller coupled to the antenna interface circuit, the directionality controller adapted to control a directionality of the antenna system.

15. The system of claim 14, further comprising a signal analyzer coupled to the transceiver and the directionality controller, the signal analyzer adapted to analyze a quality of each of one or more RF signals received by one or more of the first and second antennas, and wherein the directionality controller is adapted to control the directionality of the antenna system based on the quality of the each of the one or more RF signals.

16. The system of claim 15, wherein the signal analyzer comprises a signal strength detector adapted to measure an amplitude of the each of the one or more RF signals.

17. The system of claim 15, wherein the signal analyzer comprises a data integrity detector adapted to determine whether data contained in the each of the one or more RF signals meet predetermined quality criteria.

18. The system of claim 15, wherein the implantable medical device comprises an RF test signal generator to generate the one of more RF signals, upon receiving a command from the external device to cause the implantable medical device to operate in a telemetry testing mode.

19. The system of claim 15, wherein:
the antenna interface circuit comprises a switching circuit adapted to provide electrical connection between the transceiver and one of the first and second antennas; and
the directionality controller comprises an antenna selector adapted to control the electrical connection between the transceiver and the first and second antennas based on the quality of the each of the one or more RF signals received by each of the first and second antennas.

20. The system of claim 19, wherein the first antenna is printed on a printed circuit board housed in the external device, and the second antenna is housed in a hand-held device coupled to the external device via a cable.

21. The system of claim 19, wherein the first antenna is one of a single planar dipole antenna, a planar monopole antenna, and a loop antenna, and the second antenna is one of a planar patch antenna and a slot antenna and has a predetermined half-power beamwidth of less than about 180 degrees.

22. The system of claim 19, wherein the antenna system further comprises a third antenna, the third antenna configured to be an additional directional antenna.

23. A system for communicating with an implantable medical device, the system comprising:
an external device adapted to be communicatively coupled to the implantable medical device via radio-frequency (RF) telemetry and adapted to control operation of the implantable medical device and receive data from the implantable medical device, the external device comprising:
a transceiver;
an antenna system comprising at least two antennas each having a predetermined beamwidth;
an antenna interface circuit coupled between the transceiver and the antenna system, the antenna interface circuit comprising an antenna orientation circuit adapted to allow effective orientation of the antenna system;
a signal analyzer coupled to the transceiver, the signal analyzer adapted to analyze a quality of each of one or more RF signals received by one or more of the at least two antennas; and
a directionality controller coupled to the antenna interface circuit and the signal analyzer, the directionality controller comprising an electronic antenna steerer adapted to effectively orient the antenna system based on the quality of the each of the one or more RF signals.

24. The system of claim 23, wherein the at least two antennas comprise substantially identical planar dipole antennas.

25. The system of claim 24, wherein the at least two antennas are printed on a circuit board housed in the external device.

26. The system of claim 23, wherein the signal analyzer comprises a peak detection circuit adapted to determine an effective orientation of the antenna system at which a maximum amplitude is measured.

27. The system of claim 23, wherein the antenna interface circuit comprises a multiplier adapted to multiply weighting signals with the at least two antennas, and the electronic steerer comprises a weighting signal generator adapted to generate a plurality of weighting signals each corresponding to one of the at least two antennas to control the effective orientation of the antenna system.

28. The system of claim 23, wherein the antenna interface circuit comprises a plurality of delay lines, and the electronic steerer comprises a delay line selector adapted to control the effective orientation of the antenna system by selecting one of the plurality of delay lines to be coupled between each of the at least two antennas and the transceiver.

29. The system of claim 28, wherein each delay line of the plurality of delay lines comprises a conductive path having a predetermined length.

30. A method for communicating with an implantable medical device via radio-frequency (RF) telemetry, the method comprising:
receiving one or more RF signals from the implantable medical device using an antenna system comprising a plurality of directional antennas each having a predetermined half-power beamwidth of less than about 180 degrees;
analyzing a quality of each of the one or more RF signals; and
controlling a directionality of the antenna system based on an outcome of the analyzing.

31. The method of claim 30, further comprising sending a command to the implantable medical device to cause it to produce and send the one or more RF signals.

32. The method of claim 30, further comprising transmitting commands via the antenna system to control the operation of the implantable medical device.

33. The method of claim 32, wherein transmitting commands via the antenna system to control the operation of the implantable medical device comprises transmitting commands via the antenna system to control delivery of at least one of a pacing therapy, a cardiovertion therapy, a defibrillation therapy, a cardiac resynchronization therapy, and a drug therapy.

34. The method of claim 32, further comprising receiving at least one of data indicative of an operational status of the implantable medical device and physiological data acquired by the implantable medical device via the antenna system.

35. The method of claim 30, wherein:
receiving the one or more RF signals comprises receiving a first RF signal using an antenna of the antenna system and receiving at least one further RF signal using at least one further antenna of the antenna system;
analyzing the quality comprises analyzing a quality of each of the first and further RF signals; and
controlling a directionality of the antenna system comprises selecting one of the first and further antennas of the antenna system.

36. A method for communicating with an implantable medical device via radio-frequency (RF) telemetry, the method comprising:
receiving a first RF signal from the implantable medical device using an approximately non-directional antenna of an antenna system;
receiving a further RF signal from the implantable medical device using a directional antenna of the antenna system;
analyzing a quality of each of the first and further RF signals; and
selecting one of the approximately non-directional antenna and the directional antenna based on an outcome of the analyzing.

37. The method of claim 36, wherein:
analyzing the quality comprises:
determining a signal strength of the first RF signal;
determining a signal strength of the further RF signal; and
comparing the signal strengths of the first and further RF signals; and
selecting one of the approximately non-directional antenna and the directional antenna comprises selecting the antenna associated with the highest signal strength.

38. The method of claim 36, wherein:
each of the first RF signal and the further RF signal contains binary data;
analyzing the quality comprises:
determining data integrity of the first RF signal;
determining data integrity of the further RF signal;
determining whether the data integrity of the first RF signal satisfies a predetermined data integrity standard; and
determining whether the data integrity of the further RF signal satisfies the predetermined data integrity standard; and
selecting one of the approximately non-directional antenna and the directional antenna comprises selecting the antenna associated with an satisfactory data integrity.

39. A method for communicating with an implantable medical device via radio-frequency (RF) telemetry, the method comprising:
steering electronically an effective orientation of an antenna system comprising a plurality of antennas forming a phased-array antenna,
receiving a first RF signal from the implantable medical device using the phased-array antenna oriented at each of a plurality of effective orientations;
analyzing a quality of the first RF signal associated with the each of the plurality of effective orientations; and
selecting one of the plurality of effective orientations based on an outcome of the analyzing the quality.

40. The method of claim 39, wherein analyzing the quality comprises measuring a signal strength of the first RF signal at each of the plurality of effective orientations, and selecting one of the plurality of effective orientations comprises selecting one of the plurality of effective orientations associated with the highest signal strength.

41. The method of claim 39, wherein analyzing the quality comprises measuring a signal strength and data integrity of the first RF signal at each of the plurality of effective orientations, and selecting one of the plurality of effective orientations comprises selecting, among the one or more of plurality of effective orientations where the data integrity of the first RF signal is satisfactory, one of the plurality of effective orientations associated with the highest signal strength.

42. The method of claim 39, further comprising repeating the steering, receiving, analyzing, and selecting on a periodic basis.

43. The method of claim 39, wherein steering electronically comprises applying weighting factors to the plurality of antennas and adjusting the values of the weighting factors to steer the effective orientation of the phased-array antenna.

44. The system of claim 39, wherein steering electronically comprises controlling transmission delays associated with the plurality of antennas and adjusting the transmission delays to steer the effective orientation of the phased-array antenna.

45. The method of claim 44, wherein adjusting the transmission delays comprises selecting delay lines coupled to the plurality of antennas.

46. A method for communicating with an implantable medical device via radio-frequency (RF) telemetry, the method comprising:
receiving a first RF signal using an antenna having a directionality characteristic;
analyzing a quality of the first RF signal and determining whether the quality satisfies a predetermined signal quality standard; and
receiving at least one further RF signal from the implantable medical device using at least one further antenna having a further directional characteristic if the quality of the first RF signal does not satisfy the predetermined signal quality standard, the further antenna having the further directional characteristic is more directional on at least one plane than the antenna having the directionality characteristic.

47. The method of claim 46, further comprising:
analyzing a quality of the further RF signal;
determining whether the quality of the further RF signal satisfies the predetermined signal quality standard.

48. The method of claim 47, wherein:
the first and further RF signals each contain binary data;
analyzing the quality of the first RF signal comprises determining data integrity of the first RF signal; and
analyzing the quality of the further RF signal comprises determining data integrity of the further RF signal.

* * * * *